(12) United States Patent
Bazile et al.

(10) Patent No.: US 9,364,444 B2
(45) Date of Patent: Jun. 14, 2016

(54) FUNCTIONAL PLA-PEG COPOLYMERS, THE NANOPARTICLES THEREOF, THEIR PREPARATION AND USE FOR TARGETED DRUG DELIVERY AND IMAGING

(71) Applicant: SANOFI, Paris (FR)

(72) Inventors: Didier Bazile, Paris (FR); Patrick Couvreur, Villebon sur Yvette (FR); Harivardhan Reddy Lakkireddy, Paris (FR); Nicolas Mackiewicz, Preverenges (CH); Julien Nicolas, Igny (FR)

( * ) Notice: Subject to any disclaimer, the term of this patent is extended or adjusted under 35 U.S.C. 154(b) by 0 days.

(21) Appl. No.: 14/381,197

(22) PCT Filed: Feb. 28, 2013

(86) PCT No.: PCT/EP2013/054085
§ 371 (c)(1),
(2) Date: Aug. 26, 2014

(87) PCT Pub. No.: WO2013/127949
PCT Pub. Date: Sep. 6, 2013

(65) Prior Publication Data
US 2015/0037419 A1 Feb. 5, 2015

(30) Foreign Application Priority Data
Feb. 28, 2012 (EP) ..................................... 12305236

(51) Int. Cl.
| A61K 47/30 | (2006.01) |
|---|---|
| A61K 9/51 | (2006.01) |
| A61K 47/48 | (2006.01) |
| C07D 249/04 | (2006.01) |
| C08G 63/664 | (2006.01) |
| C08G 63/685 | (2006.01) |
| A61K 31/337 | (2006.01) |
| C08G 63/91 | (2006.01) |

(52) U.S. Cl.
CPC ................. *A61K 9/5153* (2013.01); *A61K 9/51* (2013.01); *A61K 31/337* (2013.01); *A61K 47/482* (2013.01); *A61K 47/48215* (2013.01); *C07D 249/04* (2013.01); *C08G 63/664* (2013.01); *C08G 63/6852* (2013.01); *C08G 63/91* (2013.01); *A61K 9/5138* (2013.01)

(58) Field of Classification Search
None
See application file for complete search history.

(56) References Cited

U.S. PATENT DOCUMENTS

2010/0104645 A1* 4/2010 Ali ....................... A61K 9/5153
424/489

FOREIGN PATENT DOCUMENTS

WO 2011/046946 A2 4/2011

OTHER PUBLICATIONS

Egli et al. "Functionalization of Block Copolymer Vesicle Surfaces," Polymers, 3(1):252-280 (Jan. 11, 2011).
Opsteen et al. ""Clickable" polymersomes," Chemical Communications, 30:3109-3216 (Aug. 14, 2007; published online Apr. 27, 2007).
Zhang et al. "Synthesis and Evaluation of Clickable Block Copolymers for Targeted Nanoparticle Drug Delivery," Molecular Pharmaceutics, 9(8):2228-2236 (Jun. 26, 2012).
Xiao, R.Z., "Recent advances in PEG-PLA block Copolymer nanoparticles" International Journal of Nanomedicine (2010), vol. 5, pp. 1057-1065.
Yun, Yun et al., "Functional Polylactide- g-Paclitaxel-Poly(ethylen glycol) by Azide-Alkyne click chemistry" Macromolecules (2011), vol. 44(12), pp. 4793-4800.
Natarajan, Arutselvan et al, "Construcction of Di-scFv through a Trivalent Alkyne-Azide 1,3-Dipolar Cycloaddition" Chemical Communications (2007), vol. 7(1), pp. 695-697.
Natarajan, Arutselvan et al, "Supplementary Material to Construction of Di-scFV through a Trivalent Alkyne-Azide 1,3-dipolar cycloaddtion" ChemComm (2007), retrieved from the internet: XP55039794 URL:http://www.rsc.org/suppdata/cc/b6/b611636a/b611636a.pdf.
Steinmetz, Nicole F., et al., "Buckyballs meet viral nanoparticles: candidates for Biomedicine" Journal of the American Chemical Society,( 2009), vol. 131(47), pp. 17093-17095.
Adibekian, Alexander et al., "Click-generated triazole ureas as ultrapotent in vivo-active serine hydrolase inhibitors" Nature Chemical Biology (2011), vol. 7(1), pp. 469-479.
The International Search Report of PCT/EP2013/054085 dated May 17, 2013.

* cited by examiner

*Primary Examiner* — Michael B Pallay
(74) *Attorney, Agent, or Firm* — McDonnell Boehnen Hulbert & Berghoff LLP

(57) ABSTRACT

Functional PLA-PEG copolymers, the nanoparticles thereof, their preparation and use for targeted drug delivery and imaging The present invention concerns novel functional PEG-PLA containing copolymers, the nanoparticles containing the same, their process of preparation and their use for site specific targeted drug delivery and imaging.

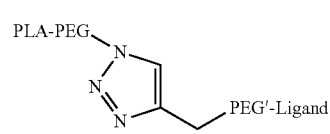

(A)

24 Claims, 4 Drawing Sheets

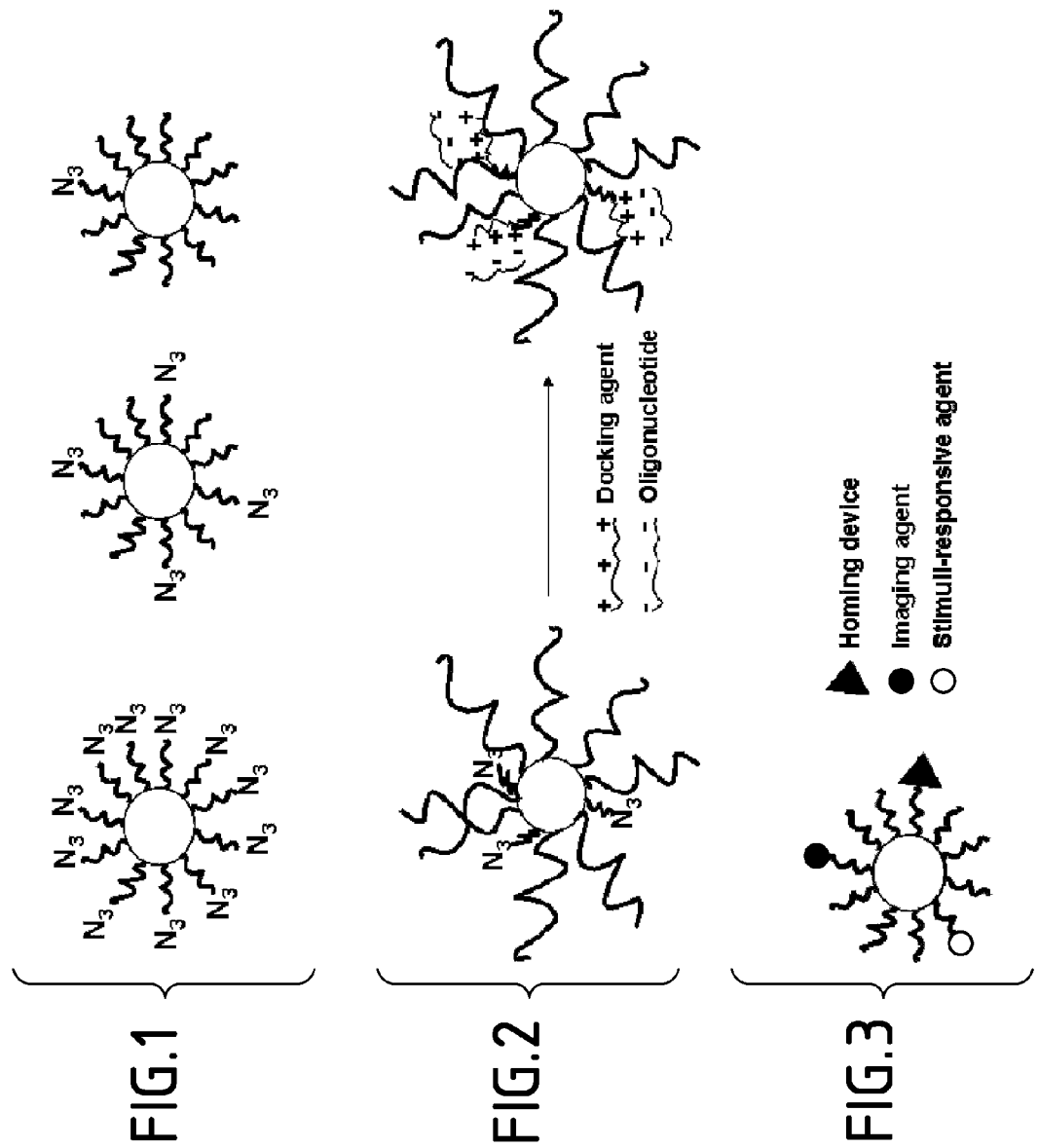

a.
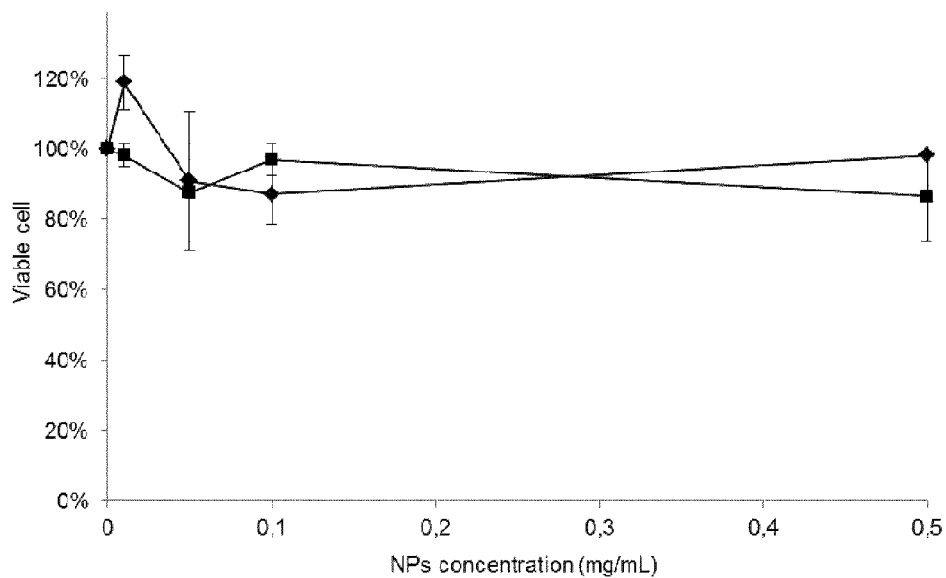
b.
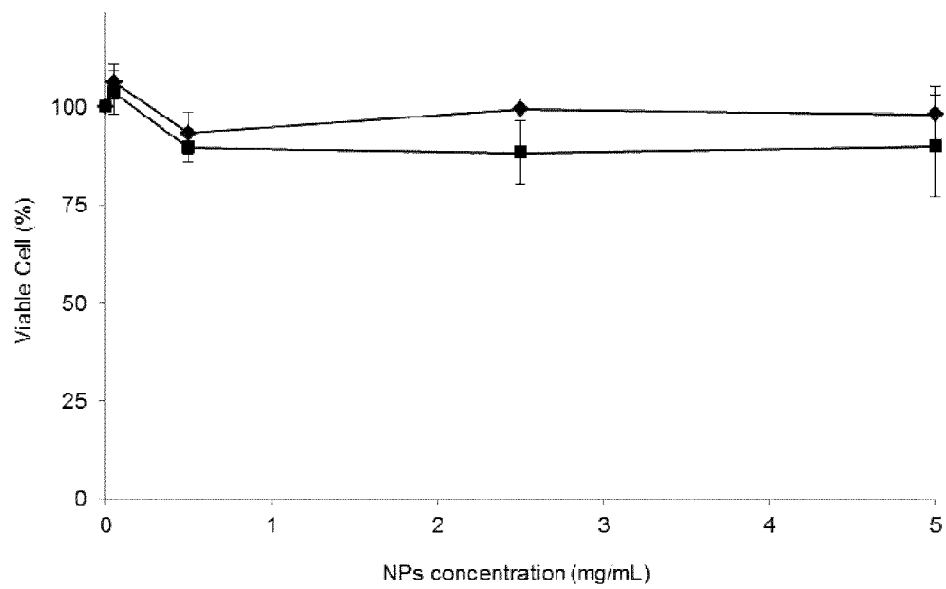
FIG.5 a.
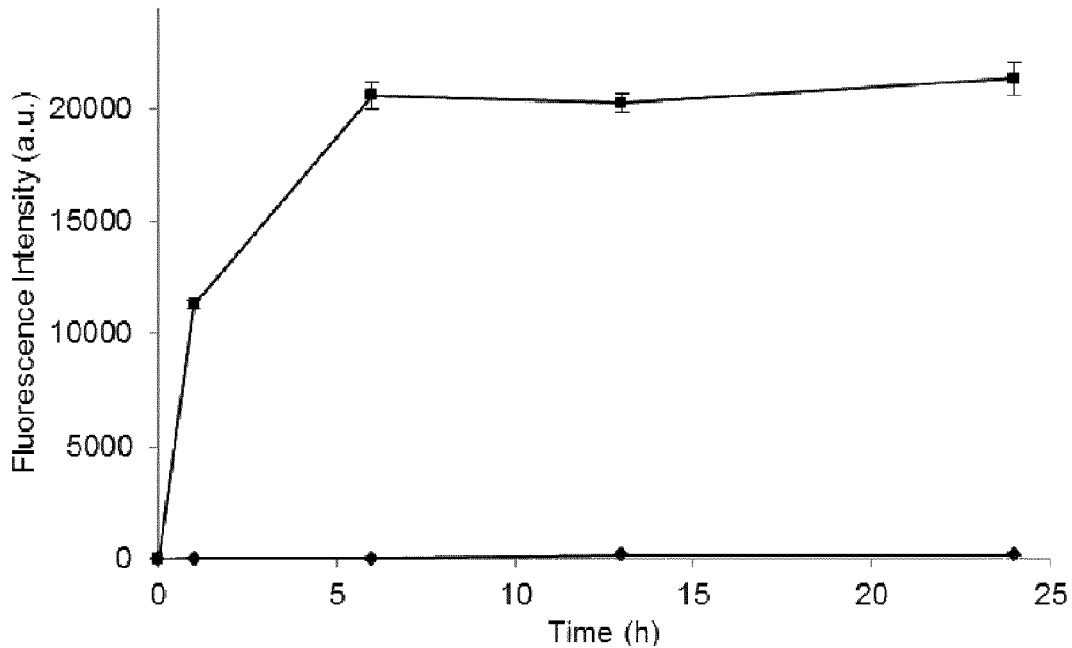
b.
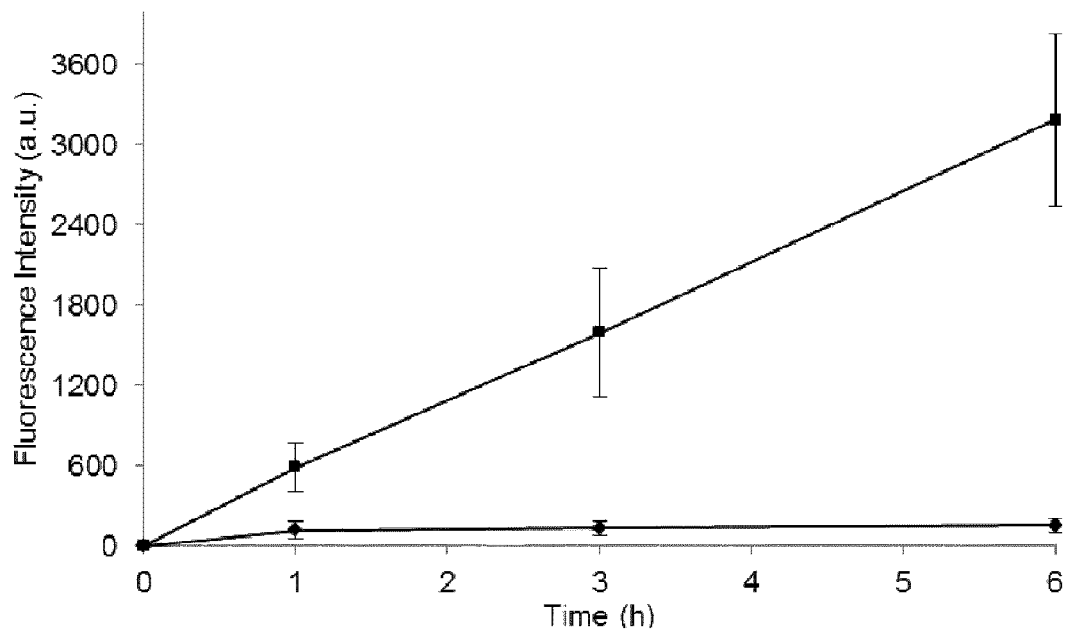
FIG.6

FUNCTIONAL PLA-PEG COPOLYMERS, THE NANOPARTICLES THEREOF, THEIR PREPARATION AND USE FOR TARGETED DRUG DELIVERY AND IMAGING

This application is a national stage application under 35 U.S.C. §371 of International Application No. PCT/EP2013/054085, filed Feb. 28, 2013, which claims priority to European Patent Application No. 12305236.7, filed Feb. 28, 2012, the disclosure of which are explicitly incorporated by reference herein.

The present invention concerns the field of targeted drug delivery and imaging and in particular the delivery by means of non-covalent encapsulation or conjugation of a drug into a poly(ethylene glycol)-poly(lactic acid) (PEG-PLA) nanoparticle.

Synthesis of PLA-PEG nanoparticles and their applications in drug delivery has been largely described in the literature. In PLA-PEG composition, PLA (poly(lactic acid)) is hydrophobic and PEG is hydrophilic. PLA-PEG assembles into nanoparticles in aqueous medium, with PLA forming the core and PEG forming the corona. Upon intravenous injection, the PEG corona in the PLA-PEG nanoparticles has been shown to protect the nanoparticle from phagocytosis ("stealth effect") and thus minimize rapid systemic clearance of nanoparticles, and thereby increase their systemic half-life (U.S. Pat. No. 5,683,723 describing nanoparticles based on polyoxyethylene and polylactic acid block copolymer). Moreover, such nanoparticles accumulate in tumor by the previously described "Enhanced Permeability and Retention" (EPR) effect. In the field of cancer in particular, tumor specific treatments are desired due to the strong side effects of chemotherapies, and in this context, polymeric nanoparticles have been considered as promising drug delivery systems. When incorporated in the PLA-PEG nanoparticles, the drugs experience prolonged systemic circulation and potentially higher concentration in the tumor due to the EPR effect. In order to deliver the nanoparticle with increased specificity to the tumor, tissue targeting/accumulation approach using homing device could be employed (Pulkkinen et al. Eur J Pharm Biopharm 70 (2008) 66-74, Zhan et al. J Control Rel 143 (2010) 136-142, Farokhzad et al. Cancer Res 64 (2004) 7668-7672, Gao et al. Biomaterials 27 (2006) 3482-3490).

The use of PLA-PEG nanoparticles further functionalized with a targeting ligand has thus been investigated by the inventors.

The use of click chemistry (Huisgen coupling) has been described in the literature for the synthesis of different polymeric (Lv et al. J Colloid Interface Sci. 356 (2011) 16-23, Jubeli et al. J Polym Sci Part A: Polym Chem. 48 (2010) 3178-3187, Lecomte et al. Macromol Rapid Commun. 29 (2008) 982-997) or metallic nanoparticle (Hanson et al. US2010/0260676 A1, 2010).

Click chemistry is of interest because this approach results in high yield, reaction conditions are easy to handle and scalable because the reaction is insensitive to oxygen and water. The background of this reaction is well-known, involves a low amount of catalyst and leads to a high coupling yield.

Recently, Deshayes et al (Pharm. Res. (2011), 28, 1631-1642) reported the conjugation of a cyclopeptide (used as a ligand binding specifically to targeting vascular endothelial growth factor (VEGF), to a polyvinylidene fluoride-poly(acrylic acid) nanoparticle by click-chemistry. Click chemistry has already been considered for synthesizing macromolecules containing both PLA and PEG polymers. Tang et al Macromolecules 2011, 44, 1491-1499 disclosed the coupling of a PEG-g-PLA-alkinyl intermediate with an azido derivative (poly(azidopropyl-L-glutamate)). Further, Yu et al. Macromolecules, 2011, 44(12), 4793-4800 recently described a nanoparticle made by the macromolecule PLA-g-paclitaxel-PEG where paclitaxel bridges the PLA backbone and PEG side chains. The drug is however not physically encapsulated into the nanoparticle and the structure does not comprise a targeting ligand. Lu et al Bioconjugate Chem 2009, 20, 87-94 also described a macromolecule containing PLA and PEG made by click chemistry and onto which a peptide (RGD=arginine-glycine-aspartate) is attached for cell targeting. The structure of the macromolecule involves the synthesis of structurally complex intermediates: the azide copolymer (poly(2-methyl-2-carboxytrimethylene-carbonate-co-D, L-lactide)-g-PEG-Azide) and the alkyne-modified KGRGDS peptides.

Zhang et al (Mol. Pharmaceutics 2012, 9, 2228-2236) disclose nanoparticles made of a macromolecule containing PLA and PEG, wherein the surface is conjugated with ligands using click chemistry, thus resulting in a ligand directly attached to the triazole group. Xiao et al (International Jounal of nanomedicine 5, 1, 2010, 1057-1065) generally concerns PEG-PLA containing nanoparticles. Arutselvan et al (Chemical Communications 7, 2007, 695-697), WO 2011/046946, Steinmetz et al Journal of the American Chemical Society 131, 47, 2009, 17093-17095) and Adibekian et al (Nature Chemical Biology 7, 2011, 469-479) disclose alkyne-PEG derivatives.

There is therefore a need to design a straightforward preparation process of PEG-PLA containing nanoparticles able to encapsulate drug for site-specific delivery on to which a desired functional ligand may be attached using click chemistry.

The present invention thus concerns the provision of PLA-PEG nanoparticles comprising an easy-to prepare PLA-PEG chain covalently bound to a targeting ligand through a linker, obtainable by click chemistry.

According to the invention, preparation of the nanoparticles involves the synthesis of a PLA-PEG-azide compound which may act as a clickable copolymer platform onto which any functional alkyne-ligand, eg. homing device, imaging agent, stimuli-responsive agent, docking agent, cell penetration enhancing agent, detoxifying agent, drug may be coupled using click chemistry by a versatile approach.

According to a first object, the present invention thus concerns a compound of formula (A)

$$\text{PLA-PEG}-\underset{N}{\underset{\|}{N}}\diagdown N \diagdown \diagup \diagdown \text{PEG'-Ligand} \qquad (A)$$

where:
PLA represents a polylactic acid rest;
PEG represents a polyethylene glycol rest;
The linker PEG' is a polyethylene glycol rest; and
Ligand is a rest of a functional ligand.

As used herein, the term "rest" refers to a divalent or monovalent radical depending on the molecule from which it derives, or of a derivative thereof.

In the general formula (A) above, the following particular embodiments may be considered or anyone of the combinations thereof:

according to an embodiment, PEG' is of formula $$(1)\diagdown \diagup O \diagdown \diagup \diagdown_{n'} (2)$$

where:
n' is the number of units and is between 1 to 10
(1) is the attachment of the bond to the —(CH$_2$)-triazole group;
(2) is the attachment of the bond to the ligand.

according to an embodiment, PLA is of formula:

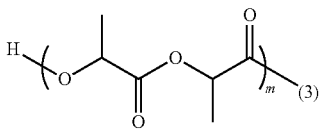

where:
(3) is the attachment of the bond to the PEG moiety; and
m is the number of units and is between 1 and 500, corresponding to a molecular weight between about 144 and 72000. In a further embodiment m is generally between 100 and 300, corresponding to a molar weight between about 14400 and 43200 g/mol.

according to an embodiment, PEG is of formula:

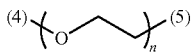

where:
(4) is the attachment of the bond to -PLA;
(5) is the attachment of the bond to the nitrogen atom of

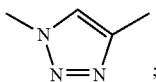

and
n is the number of units and is between 1 and 300, corresponding to a molar weight between about 44 and 13200 g/mol. In a further embodiment n is between 20 and 70, corresponding to a molar weight between about 880 and 3080 g/mol.

Binding between PLA and PEG (PLA-PEG) consists in an ester bond between the terminal carboxylic group of the PLA moiety and the terminal hydroxyl group of the PEG moiety.

Binding between PEG' and ligand (PEG'-Ligand) is not represented but it consists in an amide bond formed by the carboxylic group of the ligand and the amino group resulting from the terminal hydroxy group of PEG'.

In one embodiment, a ligand may be chosen from rests of homing devices, diagnostic agents, imaging agents, stimulisensitive agents, docking agents, cell penetrating agents, detoxifying agents, drugs. In a particular embodiment of a compound of formula (A), ligand may be chosen from anisamide, folic acid, and fluorochromes such as FP-547.

In the context of the present invention:
a halogen atom is understood to mean a fluorine, chlorine, a bromine or an iodine;
a ($C_1$-$C_6$)alkyl group is understood to mean a saturated aliphatic group which comprises from 1 to 6 carbon atoms (advantageously from 1 to 4 carbon atoms) and which is linear or branched. Mention may be made, by way of examples, of the methyl, ethyl, propyl, isopropyl, butyl, isobutyl, tert-butyl, pentyl, hexyl and the like.

The compounds of formula (A) can be provided in the form of a free base or in the form of addition salts with acids, which also form part of the invention.

These salts are advantageously prepared with pharmaceutically acceptable acids, but salts with other acids, useful for example for the purification or for the isolation of the compounds of formula (A), also form part of the invention.

The compounds of formula (A) may form nanoparticles. Thus, according to another object, the present invention also concerns a nanoparticle comprising one or more identical or different compounds of formula (A).

The expression "identical or different compounds" as used herein indicates that said compounds may have the same or have distinct formula depending on the definitions of their various PEG, PLA, PEG', R, m, n etc.

Said nanoparticles may also comprise one or more identical or different compounds of formula (I'):

where PLA, PEG are defined as in formula (A) and R is H or a $C_1$-$C_6$ alkyl, such as methyl.

Said nanoparticles may optionally comprise a drug.

The term "drug" used herein refers to therapeutic substances that may be administered to a patient in need thereof. Any relevant drug of interest (especially water-insoluble drugs) could be non-covalently encapsulated into the nanoparticle and/or covalently conjugated to the nanoparticle (optionally through a linker), to be delivered into the body.

The drug may be in particular an antibiotic, anti-cancer agent, antiviral agent, anti-inflammatory agent, a vaccine antigen or a nutraceutical.

In particular, the drug can be a cytotoxic agent, such as a taxoid and more particularly docetaxel.

Thus in one embodiment the drug is non-covalently encapsulated (such as physically encapsulated) within the nanoparticles. In another embodiment thereof the drug is covalently conjugated, optionally through a linker, to the nanoparticles, in particular where the ligand is a drug.

In a particular embodiment, the ligand is not a drug but the drug is non-covalently encapsulated in the nanoparticle.

As used herein, the term "nanoparticles" refers to particles having a mean diameter between 10 nm and 900 nm. In a further embodiment, the nanoparticles of the invention have a mean diameter between 50 and 300 nm.

They typically exhibit a polydispersity index (PdI) between 0.01 and 0.4, more specifically between 0.1 and 0.4, and have a zeta potential between −30 and +30 mV.

With a cationic ligand the zeta potential may be between 1 and 30 mV, with an anionic ligand between −30 and −1 mV.

Nanoparticles of the invention are illustrated in FIGS. 2-3.

According to the invention, said nanoparticles may be prepared by nanoprecipitation of compounds of formula (A), optionally in the presence of compounds of formula (I') above and/or optionally followed by non-covalent encapsulation or covalent conjugation of a drug.

As used herein, the term "nanoprecipitation" refers to a process comprising precipitation or emulsification and size reduction of one or more compounds in the form of nanoparticles in suspension.

Typically, said process comprises centrifugation of the suspension. The process may also include one or more steps chosen from:
preparing an organic phase of the compounds of formula (A) and optionally (I') in a suitable solvent or mixture of solvents, such as methylene chloride, ethyl acetate, acetone, ethanol, tetrahydrofuran, etc.
preparing an aqueous phase optionally stabilized with one or more stabilizing agents, such as sodium cholate, polyvinyl alcohol (PVA), poloxamer, phospholipids etc.;
mixing the organic and aqueous phases;
size reduction of the suspension (eg. by using ultrasonication);
removal of the organic phase, for example by evaporation under vacuum or under air flow;

centrifugation of the aqueous phase, in particular ultracentrifugation up to 50000 g;
collecting the nanoparticles; and/or
resuspending the obtained nanoparticles in aqueous medium.

Typically, the nanoparticles of the invention are obtained by using an aqueous miscible organic solvent (such as acetone) as the organic phase precipitated within an aqueous phase by using optionally with stabilizing agent, or by using dichloromethane or ethyl acetate as the organic phase mixed with aqueous phase containing PVA or a poloxamer or sodium cholate as stabilizing agent. Suitable Poloxoamers for use in making the nanoparticles are available under the TM Pluronic. A suitable poloxamer is poloxamer 188 (available as Pluronic® F68 or Lutrol® F68, BASF).

According to the invention, the nanoparticles made from the PLA-PEG-functional ligand may be used for a variety of purposes including the delivery of therapeutic substances (drugs) into the human body. In one embodiment of the present invention the nanoparticle further comprises a drug. In this case, the therapeutic substance is non-covalently encapsulated (physical encapsulation) into the nanoparticle matrix, and is better delivered to the intended tissue.

In another embodiment, the drug may be covalently conjugated to the compound of formula (A) e.g. in place of the ligand, optionally through a linker. The covalent conjugation may be of interest to maintain the association of the drug to the carrier in vivo, for drug delivery and imaging applications.

By mixing different compounds of formula (A) with different ligands, multifunctional nanoparticles may be obtained. These multifunctional nanoparticles may be used for combinatorial applications (see FIG. 3)

According to the invention, the nanoparticle may be prepared by nanoprecipitating one or more compounds of formula (A), and optionally (I'), optionally in the presence of a drug or different drugs (for combination therapy).

The expression "functional ligand" as used herein in a compound of formula (A) or in the nanoparticles made therewith refers to any kind of compound able to target or track the delivery of a drug into the human body, or a drug itself in particular where the drug is site-specific, such as a drug specifically binding to receptors. The functional ligands can be in particular chosen from:
compounds able to follow the uptake and distribution of the nanoparticles in a cell, a tissue, an animal, or a patient, for example through providing a label that can provide an image of the nanoparticle distribution;
chemical or biological agents, including drugs, that carry out a desired end effect of the nanoparticles, such as triggering cell death, or activating or inhibiting a receptor, an enzyme, or a gene;
receptor ligands such as an oestrogen receptor antagonist, an androgen receptor antagonist, folic acid, anisamide, an RGD peptide, antibodies, peptide targeted gene vectors, aptamers, and tumor necrosis factor.

Functional ligands may include a homing device, an imaging agent, a stimuli-sensitive agent (thermosensitive agent, pH-sensitive agent, photosensitive agent etc.), a docking agent, a cell penetration enhancing agent, a detoxifying agent, a drug etc., depending on the envisioned applications.

For instance, a homing device that recognizes and binds to a specific cell/tissue-type could be used for targeting of the drug loaded nanoparticles to the specific organ/diseased tissue of interest, which could also be referred to as 'site-specific drug targeting'. PLA-PEG-homing device nanoparticles are expected to improve the delivery of the encapsulated drug to the intended disease site, increase the local drug concentration in the targeted tissue, and at the same time, facilitate a sustained drug release. This may result in an enhanced and prolonged exposure of the diseased tissue/cells to the drug, and hence an improved therapeutic benefit and reduced side effects may be achieved. Such homing agents may be in particular chosen from membrane recognition ligands, such as anisamide (having affinity for sigma receptors), folic acid (having affinity for folate receptors overexpressed on the surface of some tumor cell lines), antibodies (such as HER2, transferrin, anti-EGFR antibodies etc.) capable of recognizing the corresponding surface antigen, RGD sequence that binds to $\alpha_v\beta_3$ integrins overexpressed on tumor angiogenic endothelium, hyaluronic acid that binds to CD44 receptors, transferrin that binds to transferrin receptors, etc.

In another instance, ligands also include those which recognize and bind to biological compounds soluble or circulating in the biological fluids (eg. vascular endothelial growth factor (VEGF)), for therapeutic or detoxification strategy.

If the functional ligand coupled onto PLA-PEG nanoparticle is an imaging agent/diagnostic agent, then the nanoparticle may be employed for imaging/diagnosis of a disease or an imperfection in the body. Such imaging/diagnostic agents may be in particular chosen from iron oxide, gadolinium complexes, indocyanin green, near infra-red fluorescent probes, positron emitters (eg. $^{18}F$, $^{68}Ga$, $^{64}Cu$).

Functional ligands such as stimuli-responsive substances may be used for guiding the PLA-PEG nanoparticles to the intended site using e.g. external magnetic field, creating local stimuli-responsive changes such as heat following irradiation by near-infra red light. Such stimuli-responsive substances may be in particular chosen from e.g. iron oxide nanoparticles, gold nanoparticles or any radiation-activable substances Functional ligands such as docking agents may be used for docking the drug (for example by ion pairing principle), to protect it from degradation and to deliver it to the appropriate location in the body. As an example, the delivery by parenteral route of oligonucleotides may be made more efficient by docking those to the Oligopeptide-coupled PEG-PLA where the oligopeptide bears an electric charge opposite to that of the oligonucleotide. Such docking agents may be in particular chosen from oligopeptides (eg. poly-lysine, poly(leucine-lysine), poly(leucine-lysine-lysine-leucine))

Functional ligands such as cell penetration enhancing agents may be used for improving the cellular uptake of the nanoparticle and hence its encapsulated drug which may lead to enhanced efficacy of the drug. Such cell penetration agents may be in particular chosen from Transactivator of transcription (TAT) sequences, penetratin, polyarginine sequences, VP22 protein sequences etc.

Functional ligands such as detoxifying agent may be used for the elimination of toxic substances from the systemic circulation. Such detoxifying agents may be in particular chosen from a variety of substances, eg. chelating agents (for metal detoxification), cobalamin, cobinamide, rhodanese enzyme (for cyanide detoxification), organophosphorus hydrolyzing enzyme (for organophosphorus detoxification), naloxone, atropine (for opioid detoxification), antibodies/antibody fragments recognizing a specific toxin.

Accordingly, a Ligand may, as mentioned above, thus be chosen from:
membrane recognition ligands selected from an oestrogen receptor antagonist, an androgen receptor antagonist, folic acid, anisamide, an antibody cabable of recognising the corresponding surface antigen such as HER2, transferrin, or anti-EGFR antibodies, a RGD sequence that binds to $\alpha_v\beta_3$ integrins overexpressed on tumor angiogenic endothelium, hyaluronic acid that binds to CD44 receptors, transferrin that binds to transferrin receptors, peptide targeted gene vectors, aptamers, and tumor necrosis factor diagnostic/imaging agents selected from iron oxide, gadolinium complexes, indocyanin green, near infra-red fluorescent probes, or positron emitters (eg. $^{18}F$, $^{68}Ga$, $^{64}Cu$), stimuli responsive substances selected from iron oxide nanoparticles, gold nanoparticles, or any radiation-activable substances, docking agents selected from oligopeptides (eg. polylysine, poly(leucine-lysine), poly(leucine-lysine-lysine-leucine), a cell penetrating agent selected from Transactivator of transcription (TAT) sequences, penetratin, polyarginine sequences, or VP22 protein sequences, a detoxifying agent selected from cobalamin, cobinamide, rhodanese enzyme, an organophosphorus hydrolyzing enzyme, naloxone, atropine, or antibodies/antibody fragments recognizing a specific toxin; or a drug selected from an antibiotic, anti-cancer agent, antiviral agent, anti-inflammatory agent, a vaccine antigen or a nutraceutical.

According to another object, the present invention also concerns the process of preparation of the compounds of formula (A) above.

Said process of preparation of a compound of formula (A) comprises coupling:
a compound of formula (I):

PLA-PEG-N$_3$             (I)

with
a compound of formula (XI):

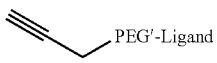
                                (XI)

where PLA, PEG, PEG', and Ligand are defined as in formula (A) above.

The coupling may be made by the so called "click chemistry". This term refers to any process wherein an azide (N3) compound is reacted with an alkyne group to form an 1,2,3-triazole.

The click chemistry coupling reaction may be carried out according to the Huisgen reaction by applying or adapting any Huisgen experimental procedure generally known by the skilled person in particular with reference to the conditions disclosed in Chem. Rev. 2008, 108, 2952-3015. Generally, said click chemistry coupling reaction is carried out according to the Huisgen reaction, either in organic or aqueous conditions.

The compounds of formula (I) may be in the form of a solution in an organic solvent or in the form of nanoparticles in an aqueous medium, optionally containing compounds of formula (I') as defined below.

In organic conditions, said click chemistry coupling reaction is typically carried out in the presence of copper(I) bromide (CuBr) and N,N,N',N',N"-pentamethyl-diethylenetriamine (PMDETA) (Chem. Rev. 2008, 108, 2952-3015). This reaction may be conducted, inter alliae, in on organic solvent such as dimethyl formamide (DMF), tetrahydrofuran (THF), toluene, dimethylsulfoxide (DMSO), at a temperature comprised between the room temperature and the reflux temperature of the reaction mixture, advantageously in anhydrous conditions. Generally, an excess of the compound of formula (XI) is used.

In aqueous conditions, said click chemistry coupling reaction is typically carried out in accordance with Chem. Rev. 2008, 108, 2952-3015, in particular in the presence of water, and copper derivatives such as CuSO$_4$-5H$_2$O. The presence of a reducing agent for the catalyst, such as sodium ascorbate may be advantageous. Generally, the aqueous conditions are used when the compounds of formula (I) are in the form of nanoparticles, in particular in an aqueous suspension.

In the click reaction, the nanoparticles comprising compounds of formula (I) may also comprise compounds of formula (I'):

PLA-PEG-OR             (I')

where PLA and PEG are defined as in formula (A) and R is H or a C$_1$-C$_6$ alkyl, such as methyl.

Compounds of formula (I') where R is methyl are for instance disclosed in U.S. Pat. No. 5,683,723.

If necessary, the nanoparticles suspension may also include a stabilizing agent, such as polyvinyl alcohol (PVA), Pluronic® (eg. Pluronic® F68) or sodium cholate.

The compounds of formula (I) involved in the preparation of the compounds of formula (A) are another distinctive object of the invention.

The present invention thus also concerns a compound of formula (I):

PLA-PEG-N$_3$             (I)

where PLA and PEG are defined as in compound of formula (A).

The compounds of formula (I) may form nanoparticles which are another object of the present invention.

Said nanoparticles may also comprise one or more identical or different compounds of formula (I'):

PLA-PEG-OR             (I')

as defined above.

Said nanoparticles are illustrated in FIG. 1.

Said nanoparticles may be obtained by nanoprecipitating one or more identical or different compounds of formula (I) as defined above, optionally in the presence of one or more identical or different compounds of formula (I').

Nanoprecipitation may be carried out according to the method disclosed above in respect of the nanoparticles comprising one or more compounds of formula (A).

The nanoparticle comprising compounds of formula (A) may also be prepared by reacting a nanoparticle comprising one or more compounds of formula (I) according to the invention and described below, with one or more compounds of formula (XI) as defined above, optionally followed by non-covalent encapsulation or covalent conjugation of a drug.

The process of the invention is highly versatile in that it allows an easy modification of the functionalities of the nanoparticles formed by the compounds of formula (A).

The process of the invention includes the possibility of altering or adjusting as desired, the density of the ligands on the surface of the nanoparticles, by mixing the compounds of formula (I) with PLA-PEG copolymer in different ratios so as to prepare nanoparticles comprising compounds of formula (I) or (A) together with PLA-PEG copolymers that are not functionalized by an azide group (see FIG. 1), said nanoparticles being then reacted with the compounds of formula (XI).

The process of the invention allows the use of compounds of formula (I) or (A) using different PEG and PLA chain lengths (see FIG. 2) for various applications. For instance, therapeutic substances that are sensitive to degradation in systemic compartment (e.g. oligonucleotides), may be coupled through a docking agent Ligand to the PLA-PEG containing short chain length PEG and then mixed with PLA-PEG copolymer made of long chain PEG, so that long chain PEG forms a brush like surface in which the therapeutic substance is masked and thereby protected from rapid degradation in systemic circulation.

Besides, the process of the invention allows combining different PLA-PEG-functional ligand types (e.g. PLA-PEG-homing device+PLA-PEG-imaging agent+PLA-PEG-stimuli responsive substance) for the formation of multifunctional nanoparticles for combinatorial applications (see FIG. 3).

The compounds of formula (I) are pivotal to the invention as they act as a clickable biodegradable copolymer platform, onto which any alkyne-functional ligand could be coupled using click chemistry (by means of the compounds of formula (XI)), for a variety of applications depending on the type of functional ligand, such as drug delivery, imaging, detoxification, etc. Thus, the advantages of the present invention include inter alliae the flexibility of synthesizing a variety of functional ligand-coupled copolymer nanoparticles that could be administered by parenteral route. In addition, the functional ligand density on nanoparticle surface may be adjusted by mixing appropriate ratios of compounds of formula (I) and compounds of formula (I'). Besides, the nanoparticles may be constructed so as to possess different chain length PEG moieties, to facilitate the intravenous delivery of therapeutic substances that are chemically sensitive in systemic circulation. Furthermore, the click reaction for coupling the functional ligand can be performed either prior to the nanoparticle formation or onto the preformed nanoparticle, depending on the chemical nature of the ligand.

According to a further object, the present invention also concerns a process for the preparation of a compound of formula (I), comprising the step of reacting a compound of formula (II):

H-PEG-X          (II)

where PEG is defined as in formula (A), and X represents either the azide ($N_3$) function or a halogen, such as a Br atom, with the lactide compound of formula:

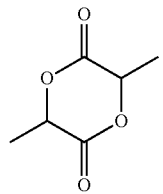

followed when X is a halogen atom, by reacting the obtained compound of formula (III):

PLA-PEG-Hal          (III)

where PLA and PEG are defined as in formula (A), and Hal represents an halogen atom, such as Br, with $NaN_3$.

This reaction with the lactide is generally carried out by ring opening polymerization (ROP). Typically, this reaction is carried out in the presence of $Sn(Oct)_2$. It may be conducted in bulk, generally under heating, or in a suitable organic solvent with a high boiling point such as toluene or xylene.

Generally, the quantity of the lactide compounds depend on the desired n in the compound of formula (I) knowing that the reaction can be always stopped before completion. Typically, the molar ratio between the PEG macro-initiator and the catalyst $Sn(Oct)_2$ is comprised between 1 and 10.

The reaction is preferably conducted under anhydrous conditions and/or at a temperature comprised between the room temperature and the reflux temperature of the reaction mixture.

The reaction with $NaN_3$ is generally conducted in an aprotic organic solvent such as DMF, dimethyl acetamide (DMA), acetone etc., with an excess of $NaN_3$.

The compound of formula (II):

H-PEG-X          (II)

may be prepared from a compound of formula (IV):

Pg-PEG-OH          (IV)

where Pg represents an hydroxyl protecting group, such as benzyl (phenyl-$CH_2$—) and PEG is defined as in formula (A) by a substitution reaction, followed by a deprotection reaction.

A protecting group Pg, as mentioned hereafter, corresponds to a group which enables, on the one hand, the protection of a reactive function such as an hydroxy or an amine during a synthesis step and, on then other hand, to recover the intact reactive function at the end of the synthesis step. Examples of protecting groups, as well as methods for protecting and deprotecting various functional groups, are given in P. G. M. Wuts and T. W. Greene, Greene's Protective Groups in Organic Synthesis, 4. ed. (2007), John Wiley & Sons and in J. F. W. McOmie, Protective Groups in Organic Chemistry, Plenum Press, 1973.

The substitution reaction comprises substituting the OH group with either an halogen atom or an azide group, by means of the appropriate reagent, such as N-halogenosuccinimide (e.g. N-bromosuccinimide (NBS)) or sodium azide, respectively.

Where a halogen group is to be substituted, this reaction is generally conducted with the appropriate N-halogenosuccinimide reagent, with $PPh_3$ in a suitable organic solvent, such as dichloromethane.

Where an azide group is to be substituted, an initial substitution with a leaving group may be conducted, as follows:
1) substituting the OH group of the compound of formula (IV) with a leaving group,
2) substituting the leaving group of the obtained compound in step 1) with an azide ($N_3$) group.

As used herein, a "leaving group" corresponds to a group which may easily be cleaved from a molecule by breaking a heterolytic bond ((ie) a bond the fission of which generates a cation and an anion), with departure of electronic pair. This group may then easily be replaced by another functional group, during a substitution reaction, for example. Such leaving groups may consist in halogen atoms or activated hydroxy groups, such as mesylate, tosylate, triflate or acetyl groups, etc. Examples of leaving groups, as well as references relating to their preparation, are given in <<Advances in Organic Chemistry>>, J. March, $3^{rd}$ Edition, Wiley Interscience, p. 310-316.

For example, in step 1), the leaving group is a mesylate and thus the substitution is carried out in the presence of mesylchloride (MsCl). This reaction is typically conducted in the presence of DMAP, in an organic solvent such as dichloromethane.

The substitution of the leaving group with the azide group in step 2) can be carried out in the presence of sodium azide, in a suitable organic solvent such as DMF.

The deprotection step comprises hydrolyzing the protecting group Pg of the substituted halogeno or azido compound obtained, so as to obtain the compound of formula (II).

The hydrolysis is typically carried out in acidic conditions, according to well-known procedures, in particular using concentrated HCl when Pg- is Phenyl-CH$_2$—.

According to a further object, the present invention also concerns a compound of formula (XI):

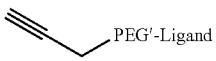
(XI)

where PEG' and Ligand are defined as in formula (A).

In particular, the present invention concerns compounds of formula (XI) with the exception of

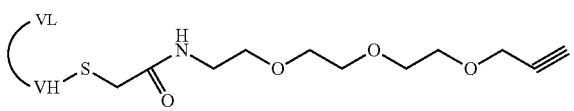

According to a further object, the present invention also concerns a process for the preparation of a compound of formula (XI):

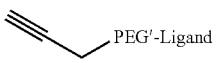
(XI)

comprising coupling
a compound of formula (XII);

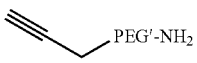
(XII)

with
a Ligand Precursor
where PEG' and Ligand are defined as in formula (A) above.

A "Ligand Precursor" is a compound which, when reacted with the —NH$_2$ group of a compound of formula (XII) leads to the group -Ligand, where Ligand is a rest of a functional ligand as defined in formula (A).

Said coupling may be carried out in the presence of a peptide coupling reagent, in the presence of a base.

Said peptide coupling agent may be chosen from known peptide coupling agents and more particularly from PyBOP (benzothiazol-1-yl-oxytripyrrolidinophosphonium hexafluorophosphate) or EDC/NHS (1-ethyl-3-[3-dimethylaminopropyl]carbodiimide hydrochloride/N-hydroxy sulfosuccinimide).

The base may be any organic or mineral base, more particularly a mineral base such as triethylamine (TEA) or N,N-diisopropylethylenediamine (DIPEA).

As for particular combinations, in one embodiment, PyBOP (benzothiazol-1-yl-oxytripyrrolidino-phosphonium-hexafluorophosphate) is used with N,N-diisopropylethylenediamine (DIPEA) and, in another embodiment, EDC/NHS (1-ethyl-3-[3-dimethylaminopropyl]carbodiimide hydrochloride/N-hydroxy sulfosuccinimide) is used with triethylamine.

The reaction may be conducted in a suitable organic solvent such as dichloromethane, DMF or dimethyl sulfoxide (DMSO).

Representative ligand precursors include:

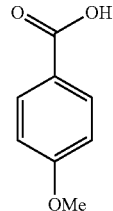 [SMILES: COc1ccc(C(=O)O)cc1]

which is an anisamide precursor, leading to Ligand-=

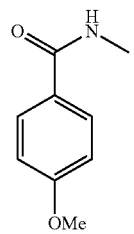

being a rest of anisamide;
folic acid;
FP-547-NHS leading to Ligand-=—NH—C(=O)—(CH$_2$)$_2$-FP547 being a rest of FP547.

According to an embodiment, the compound of formula (XII) may be prepared by:
reacting a compound of formula (XIII):

H-PEG'-OH (XIII)

with a compound of formula (XIV):

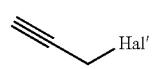
(XIV)

and a base,
where PEG' is defined as in formula (A) and Hal' represents a halogen atom such as Br,
to form the compound of formula (XV):

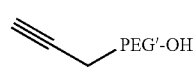
(XV)

followed by:
transforming the compound of formula (XV) into the compound of formula (XII).

The reaction of the compound of formula (XIII) with the compound of formula (XIV) is generally conducted in the presence of a strong base, such as NaH, in a suitable organic solvent such as DMF.

The transformation of the compound of formula (XV) into the compound of formula (XII) may be achieved by various methods.

In particular, it may comprise:

reacting the compound of formula (XV) with phthalimide and PPh₃ to form the compound of formula (XVI):

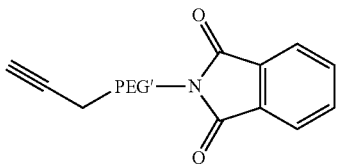

(XVI)

followed by:

reacting the compound of formula (XVI) with hydrazine hydrate to form the compound of formula (XII).

The reaction of the compound of formula (XV) with phthalimide and PPh₃ is generally conducted in a suitable organic solvent such as THF, in the presence of diisopropyl azodicarboxylate (DIPAD), typically at room temperature.

The reaction of the obtained compound of formula (XVI) with hydrazine hydrate (N₂H₄.H₂O) can be carried out in ethanol as solvent.

Alternatively, the transformation of the compound of formula (XV) into the compound of formula (XII) comprises:

reacting the compound of formula (XV) with a compound of formula (XVII):

Lg-Hal″ (XVII)

where Lg is a leaving group and Hal″ is a halogen atom, to form the compound of formula (XVIII):

(XVIII)

followed by:

reacting the obtained compound of formula (XVIII) with hydrazine hydrate (N₂H₄.H₂O) and potassium phthalate, to form the compound of formula (XII).

In formula (XVII), Lg is advantageously a methanesulfonyl group (Ms) and Hal″ may be a Cl atom.

This reaction is generally conducted in the presence of a base, such an organic base, eg triethylamine (Et₃N), and optionally a catalyst such as dimethylaminopyridine (DMAP) and/or in a suitable organic solvent such as dichloromethane.

The reaction of the obtained compound of formula (XVIII) is generally conducted by first adding potassium phthalate and catalytic amounts of sodium iodide (NaI) in a solvent such as DMF, followed by removing the solvent and adding hydrazine hydrate (N₂H₄.H₂O) in a solvent such as ethanol.

According to a further embodiment, the compound of formula (XII) may also be prepared by:

reacting a compound of formula (XIX):

H-PEG′-N₃ (XIX)

with a compound of formula (XIV):

 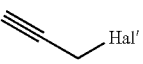

(XIV)

where Hal′ is a halogen atom, such as Br and PEG′ is defined as in formula (A), so as to form the compound of formula (XX):

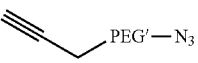

(XX)

followed by:

reacting the compound of formula (XX) with triphenylphosphine (PPh₃), leading to the compound of formula (XII).

The reaction of a compound of formula (XIX) with a compound of formula (XIV) is generally conducted in the presence of a base, such as NaH, in an organic solvent such as DMF.

The reaction of the compound of formula (XX) with triphenylphosphine (PPh₃) is generally carried out in a solvent such as tetrahydrofuran (THF), optionally in the presence of water.

The compound of formula (XIX) may be prepared from the compound of formula (XXI):

Pg-PEG′-OH (XXI)

where Pg is defined as in formula (IV), by a substitution reaction, followed by a deprotection reaction.

The substitution and deprotection reactions may be carried out as in respect of compound (II) as discussed above.

The process of the invention may also comprise the step of isolating or purifying the obtained compounds following each step if desired or required and/or conducting the desired steps in sequence.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography.

In the processes above, starting compounds and reactants, unless otherwise indicated, are commercially available or described in the literature, or can be prepared according to methods described in the literature, as disclosed in the examples below or as known to one skilled in the art.

Variations on the processes described above will be appreciated by the skilled artisan as necessary and are also part of the invention. The appropriate modifications and substitutions are readily apparent and well-known or readily obtainable from the scientific literature to those skilled in the art. In particular, such methods can be found in R. C. Larock, *Comprehensive Organic Transformations*, VCH publishers, 1989.

The compound of formula (A) or the nanoparticles comprising at least compound of formula (A) of the invention can be useful for the preparation of medicaments.

Therefore, another object of the invention is a medicament, which comprises at least one compound of formula (A), optionally in the form of a nanoparticle of the invention.

Another object of the invention is also a pharmaceutical composition, which comprises, as active principle, a compound of formula (A) optionally in the form of a nanoparticle of the invention with one or more pharmaceutically acceptable excipients.

These pharmaceutical compositions comprise an effective dose of at least one compound (A) according to the invention, and at least one pharmaceutically acceptable excipient.

Said excipients are chosen according to the pharmaceutical form and the administration route desired, among usual excipients known by the skilled in the art.

In the pharmaceutical compositions according to the invention for the oral, sublingual, sub-cutaneous, intramuscular, intra-venous, intra-arterial, topical, local, intratracheal, intranasal, transdermal or rectal administration, the active principle can be administered as a unitary dosage form, in blend with usual pharmaceutical excipients, to animals and human beings.

The appropriate unitary dosage forms comprise the oral forms, such as tablets, hard or soft gelatin capsules, powders, granules and oral solutions or suspensions, the sublingual, buccal, intratracheal, intraocular, intranasal forms, by inhalation, the topical, transdermal, sub-cutaneous, intramuscular, intra-venous or intra-arterial forms, the rectal forms and the implants. For the topical application, the compounds of the invention may be used as creams, gels, ointments or lotions.

As an example, a unitary dosage form for a compound according to the invention, in the form of a tablet, can comprise the following ingredients:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropyl methylcellulose | 2.25 mg |
| Magnesium stearate | 3.0 mg |

In specific cases, higher or lower dosages may be appropriate; these dosages are comprised within the scope of the present invention. According to usual practice, the dosage suitable to each patient is determined by the physician according to the administration route, the weight and response of the patient.

FIGURES

FIG. 1 illustrates a PLA-PEG-$N_3$ clickable nanoparticles surface exposed with different density of $N_3$. The $N_3$ density on the nanoparticle surface can be altered as desired by mixing an appropriate ratio of PLA-PEG-$N_3$ with PLA-PEG copolymer.

FIG. 2 illustrates a PLA-PEG clickable nanoparticle synthesized using different PEG chain lengths (shorter and longer) to facilitate the loading and intravenous delivery of chemically sensitive substances (eg. oligonucleotides).

FIG. 3 illustrates a multifunctional nanoparticle prepared by mixing a variety of PLA-PEG-functional ligand copolymers in appropriate ratios for combinatorial applications (eg. a nanoparticle containing homing device, imaging agent, stimuli-responsive agent).

FIG. 5a illustrates the In vitro cytotoxicity of PLA-PEG-Folic acid nanoparticles (■=51) comparatively to PLA-PEG-OMe nanoparticles (♦=S2) on KB-3-1 cells over-expressing the folate receptors.

FIG. 5b illustrates the In vitro cytotoxicity of fluorescent PLA-PEG-anisamide nanoparticles (■=S3) comparatively to the fluorescent PLA-PEG-OMe nanoparticles (♦=S4) on PC-3 cells expressing the sigma receptors.

FIG. 6a illustrates the cell penetration ability of the fluorescent PLA-PEG-Folic acid nanoparticles (■=S3') and the fluorescent PLA-PEG-OMe nanoparticles (♦=S4') on KB-3-1 cells over-expressing the folate receptors.

FIG. 6b illustrates the cell penetration ability of the fluorescent PLA-PEG-Folic acid nanoparticles (■=average of S1', S3' and S5') and the fluorescent PLA-PEG-OMe nanoparticles (♦=average of S2', S4' and S6') on KB-3-1 cells over-expressing the folate receptors. The fluorescence signals have been rationalized relative to the fluorescence of each sample prior to the experiment.

EXAMPLES

Figure 4:
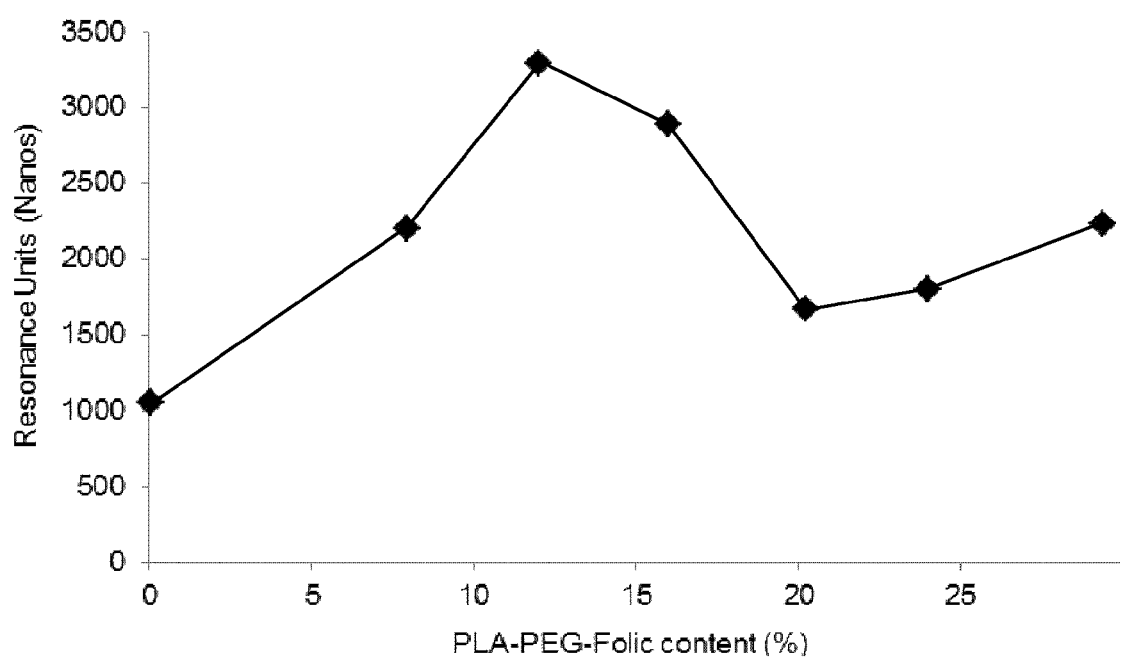
FIG. 4 represents the evaluation of the receptor binding ability of PLA-PEG-Folic acid nanoparticles using surface Plasmon resonance experiments. The graph indicates the evolution of the specific signal (resonance unit, noted RU) relative to the concentration of folic acid in the PLA-PEG-folic acid nanoparticles.

The following examples describe the synthesis of some compounds according to the invention. These examples are not intended to be limitative and only illustrate the present invention. The numbers of the exemplified compounds refer to those in the table given later, which illustrate the chemical structures and the physical properties of a number of compounds according to the invention.

Abbreviations:
MTS 3-(4,5-dimethylthiazol-2-yl)-5-(3-carboxymethoxyphenyl)-2-(4-sulfophenyl)-2H-tetrazolium
ACN Acetonitrile
$N_3$ Azide
Bz Benzyl
PyBOP (Benzotriazol-1-yloxy)tripyrrolidinophosphonium hexafluorophosphate
CuBr Copper(I) Bromide
$CuSO_4$ Copper(II) Sulfate
cHex Cyclo-hexane
Da Dalton
DCM Dichloromethane
$Et_2O$ Diethyl Ether
DIAD Diisopropyl azodicarboxylate
DMSO Dimethyl sulfoxide
DMAP Dimethylaminopyridine
DMF Dimethylformamide
DMEM Dulbecco's Modified Eagle's Medium
DLS Dynamic Light Scattering
EPR Enhanced Permeability and Retention
equiv., Eq. Equivalent
EtOH Ethanol
AcOEt Ethyl Acetate
EDTA Ethylenediaminetetraacetic acid
FBS Fetal Bovine Serum
FC Flow Channel
FP-547 Fluoprobe-547
FBP Folate Binding Protein
HPLC High-Performance Liquid Chromatography
$N_2H_4.H_2O$ Hydrazine hydrate
HBr Hydrobromic acid HCl Hydrochloric acid
IgG Immunoglobulin G
MgSO$_4$ Magnesium sulfate
MsCl Methanesulfonyl Chloride
MeOH Methanol
Ome Methoxy
EDC N-(3-Dimethylaminopropyl)-N'-ethylcarbodiimide hydrochloride
PMDETA N,N,N',N'',N''-Pentamethyldiethylenetriamine
DIEA N,N-Diisopropylethylamine
NP Nanoparticle
NBS N-Bromosuccinimide
NHS N-Hydroxysuccinimide
NMR Nuclear Magnetic Resonance
Mn Number-average Molecular Weight
PBS Phosphate Buffer Saline
PLA Poly(D,L-Lactic Acid)
PLGA Poly(D,L-lactide-co-glycolide)
PEG Poly(Ethylene Glycol)
PdI Polydispersity Index
PVA Poly(vinyl alcohol)
R.U. Resonance Unit
ROP Ring Opening Polymerization
RPMI Roswell Park Memorial Institute
SEC Size Exclusion Chromatography
NaN$_3$ Sodium Azide
NaCl Sodium Chloride
NaCh Sodium Cholate
NaH Sodium Hydride
NaOH Sodium Hydroxyde
NaI Sodium Iodide
Sn(Oct)$_2$ Stannous Octoate
SPR Surface Plasmon Resonance
THF Tetrahydrofuran
Et$_3$N (TEA) Triethylamine
PPh$_3$ Triphenylphosphine
Mw Weight-average Molecular Weight Example 1

Preparation of Precursors for Making Nanoparticles

Preparation 1: Synthesis of a Compound of Formula (XII)
1. Procedure for the Synthesis of Mono-Alkyne Polyethylene Glycol (Preparation 1A)

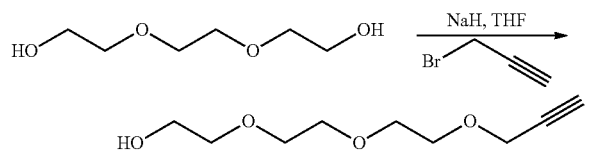

Experimental Procedure:
Triethylene glycol (Sigma-Aldrich, 5620 mg, 37.4 mmol, 1 equiv.) was dissolved in anhydrous THF (50 mL) and the resulting solution was cooled to 0° C. in dry conditions. Sodium hydride (988 mg, 1.1 equiv.) was added slowly followed by drop wise addition of propargyl bromide (80 wt. % in toluene, 4360 µL, 1.1 equiv.). The reaction was stirred for 12 hrs at room temperature under inert atmosphere.
Treatment Process:
THF was removed under reduced pressure and the residue was taken into methylene chloride (dichloromethane, DCM) and washed several times with brine. The resulting organic layer was dried over magnesium sulfate (MgSO$_4$), filtered, concentrated under reduced pressure and dried under vacuum. The crude product was purified by column chromatography over silica (eluent: cyclohexane (cHex)/ethyl acetate (AcOEt): 8/2) and 3.31 g of a yellow oil was recovered (47% yield).
NMR Characterization:
$^1$H NMR (300 MHz, CDCl$_3$) δ 4.15 (d, J=2.4 Hz, 2H), 3.70-3.60 (m, 10H), 3.57-3.53 (m, 2H), 2.70 (m, 1H), 2.41 (t, J=2.4 Hz, 1H).

2. The Synthesis of the Phthalimide-Alkyne Triethylene Glycol Compound has been Done Using Two Different Pathways, Either by One-Step or by Two-Step Via a Mesylate Intermediate.

2a) One-Step Procedure for the Synthesis of Phthalimide-Alkyne Triethylene Glycol (Preparation 1B)

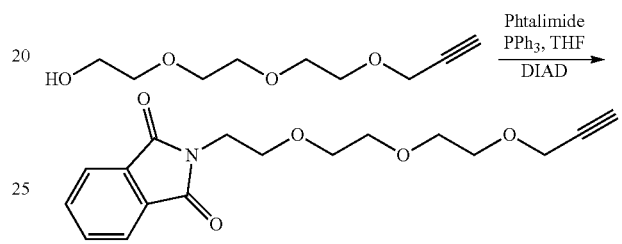

Experimental Procedure:
Preparation 1A (2000 mg, 10.6 mmol, 1 equiv.), phthalimide (2345 mg, 1.5 equiv) and triphenylphosphine (4179 mg, 1.5 equiv) were dissolved in anhydrous THF (50 mL) in dry conditions. Diisopropyl azodicarboxylate (DIAD) (3.14 mL, 1.5 equiv.) was added slowly and the reaction was stirred for 48 hrs at room temperature under inert atmosphere.
Treatment Process:
THF was removed under reduced pressure and the residue was taken into DCM and washed several times with brine. The resulting organic layer was dried over MgSO$_4$, filtered, concentrated under reduced pressure and dried under vacuum. The crude product was purified by column chromatography over silica (eluent: cHex/AcOEt: 8/2) and 3.37 g of a yellow oil was recovered (60% yield).
NMR Characterization:
$^1$H NMR (300 MHz, CDCl$_3$) δ 7.76 (dd, J=5.4, 3.1 Hz, 2H), 7.64 (dd, J=5.4, 3.1 Hz, 2H), 4.08 (d, J=2.4 Hz, 2H), 3.74 (dt, J=11.4, 6.0 Hz, 4H), 3.60-3.50 (m, 8H), 2.38 (t, J=2.4 Hz, 1H).

2b) For the Two-Step Synthesis of Phthalimide-Alkyne Triethylene Glycol, the Mesylate was first Synthesized as Follows:
Procedure for the Synthesis of Mesyl-Alkyne Triethylene Glycol (Preparation 1C)

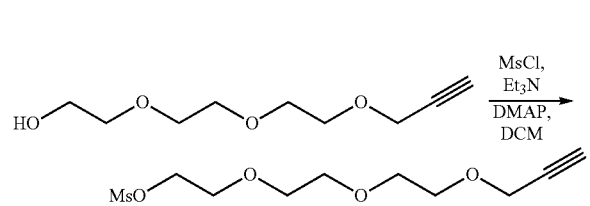

Experimental Procedure:
To a solution of alkyne triethylene glycol (preparation 1A, 4 g, 212 mmol, 1 equiv.) in DCM 60 mL) was added under inter atmosphere a catalytic amount of DMAP, methanesulfonyl chloride (3.3 mL, 2 equiv.) and triethylamine (5.9 mL, 2 equiv.) drop wise. The reaction was stirred for 4 hrs at room temperature.
Treatment Process:

The solution was washed with brine (thrice with 50 mL), the aqueous phase was then extracted with DCM (50 mL) and the combined organic layers were dried over MgSO$_4$, filtered and concentrated under reduced pressure.

The final product was directly involved (without characterization) in the following step.

2c) Procedure for the Synthesis of Phthalimide-Alkyne Triethylene Glycol (Preparation 1 D)

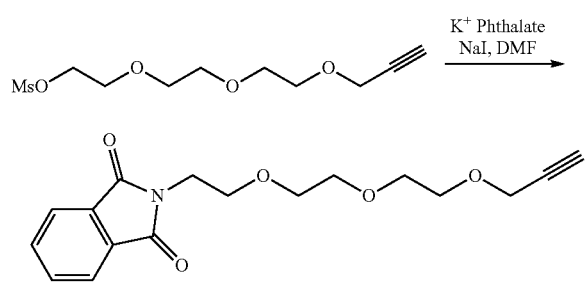

Experimental Procedure:

To a solution of mesyl-alkyne triethylene glycol (Preparation 10, 5.1 g, 19.2 mmol, 1 equiv.) in DMF (100 mL) was added potassium phthalate (7.87 g, 2.2 equiv.) and a catalytic amount of sodium iodide (less than one equivalent, e.g. a spatula tip). The solution was stirred at 80° C. overnight and the solvent was removed under reduced pressure.
Treatment Process:

The resulting residue was purified by column chromatography over silica (eluent: cHex/AcOEt: 2/8 to 4/6). 5.7 g of yellow oil were recovered (94% yield).
NMR Characterization:

$^1$H NMR (300 MHz, CDCl$_3$) δ 7.81 (dd, J=5.5, 3.0 Hz, 2H), 7.69 (dd, J=5.5, 3.0 Hz, 2H), 4.13 (d, J=2.4 Hz, 2H), 3.80 (dt, J=11.4, 6.0 Hz, 4H), 3.65-3.56 (m, 8H), 2.40 (t, J=2.4 Hz, 1H).

3) Procedure for the Synthesis of Amino-Alkyne Triethylene Glycol (Preparation 1E)

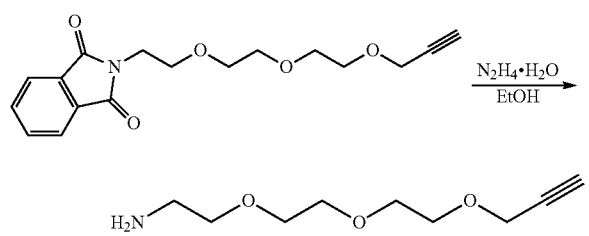

Experimental Procedure:

Preparation 1B (2034 mg, 6.4 mmol, 1 equiv.) was dissolved in ethanol (EtOH) (200 mL) and hydrazine hydrate (3.1 mL, 10 equiv) was added. The reaction mixture was stirred overnight under reflux conditions.
Treatment Process:

The reaction was cooled down to room temperature and 8 mL of concentrated hydrochloric acid were added to the reaction (pH-2-3). The precipitate was removed by filtration and the pH was raised above 10 using NaOH (2 M). The aqueous phase was extracted thrice with DCM. The resulting organic layer was dried over MgSO$_4$, filtered, concentrated under reduced pressure and dried under vacuum. 911 mg of yellow oil was recovered (76% yield).
NMR Characterization:

$^1$H NMR (300 MHz, CDCl$_3$) δ 4.13 (d, J=2.4 Hz, 2H), 3.69-3.50 (m, 8H), 3.43 (t, J=5.2 Hz, 2H), 2.79 (t, J=5.2 Hz, 2H), 2.38 (t, J=2.4 Hz, 1H), 1.33 (s, 2H). $^{13}$C NMR (75 MHz, CDCl$_3$) δ 79.64, 74.53, 73.47, 70.59, 70.40, 70.25, 69.09, 58.37, 41.80.

Preparation 2: Synthesis of a Compound of Formula (XI)

1) Procedure for the Synthesis of Anisamide-Alkyne Triethylene Glycol (Preparation 2A)

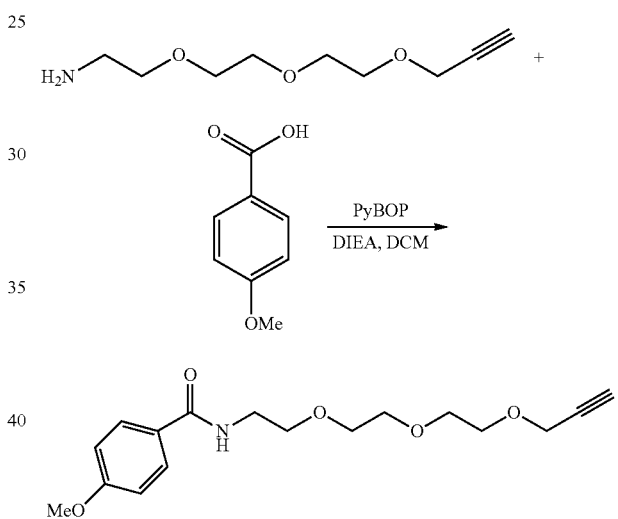

Experimental Procedure:

To a solution of Preparation 1E (200 mg, 1.07 mmol, 1 equiv.) in DCM (20 mL) was added, under inert atmosphere, PyBOP (780 mg, 1.4 equiv.), p-methoxybenzoic acid (229 mg, 1.4 equiv.) and DIEA (260 μL, 1.4 equiv.). The reaction was stirred overnight at room temperature
Treatment Process:

The solution was washed with brine (thrice with 20 mL), the aqueous phase was then extracted with DCM (20 mL) and the combined organic layers were dried over magnesium sulfate, filtered and concentrated under reduced pressure. The crude product was purified by column chromatography over silica (eluent: cHex/AcOEt: 5/5 to 7/3) and 300 mg of yellow oil were recovered (90% yield).
NMR Characterization:

$^1$H NMR (300 MHz, CDCl$_3$) δ 7.74 (d, J=8.8 Hz, 2H), 6.87 (d, J=8.9 Hz, 2H), 6.84 (broad, 1H), 4.14 (d, J=2.4 Hz, 2H), 3.81 (s, 3H), 3.71-3.53 (m, 12H), 2.42 (t, J=2.4 Hz, 1H).

2) Procedure for the Synthesis of Folic Acid-Alkyne Triethylene Glycol (Preparation 2B)

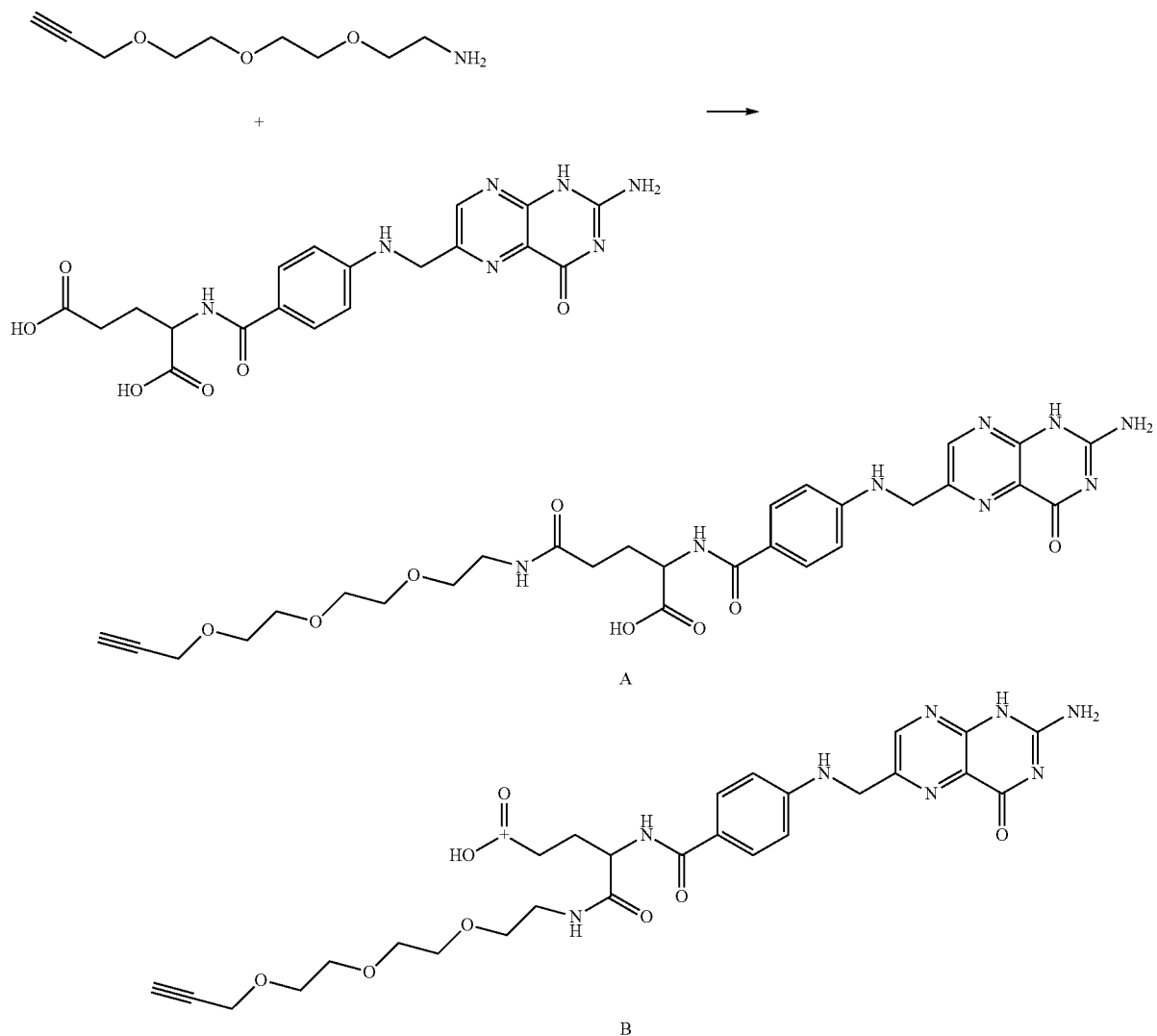

A

B

Experimental Procedure:

To a solution of preparation 1E (319 mg, 1.70 mmol, 1 equiv.) in DMF (70 mL) was added, under inert atmosphere, EDC (393 mg, 1.2 equiv.), NHS (236 mg, 1.2 equiv.) and few drops of triethylamine (Et₃N). The reaction was heated up at 50° C. and folic add (Sigma-Aldrich, 754 mg, 1 equiv.) was added to the reaction mixture. The reaction was then stirred overnight at 50° C.

Treatment Process:

The solution was concentrated under reduced pressure. The residue was precipitated into DCM and acetone, filtered and dried under vacuum.

The obtained product is analyzed on a reverse phase column (C18, Kromasil 10 μm, 4.6×250 mm) for example using a 5 to 95% acetonitrile gradient in ammonium acetate buffer (adjusted to pH 5) 20 mM in 20 min, then 95% acetonitrile for 5 min.

The product is solubilized in 20% DMF in the eluant. Purification is carried out on Kromasil C18 10 μm packed in a 100 mm column (1.5 kg of phase) and elution in a 85% ammonium acetate buffer pH 5, 20 mM and 15% acetonitrile 200 mg of raw product are eluted at the same time as the DMF injection peak.

Purification Process (Compound B):

The final purification is done by solubilizing 200 mg of the raw product using preparative HPLC with a reverse phase column Waters XBridge C18 (30×100 mm), 5 μm.

The product is first dissolved in DMSO (5 mL) and 5 mL of buffer solution (ammonium carbonate 10 mM adjusted to pH 9.3 with a 28% ammoniacal aqueous solution).

10 injections of 1 ml were done using a gradient going from 95:5 (Buffer solution (ammonium carbonate)/Acetonitrile) to 5:95 in 12 min at 30 mL/min.

NMR Characterization (Compound B):

$^1$H NMR (400 MHz, DMSO, $d_6$) δ 12.0-11.0 (broad s, 1H), 8.61 (s, 1H), 8.29 (broad s, 1H), 7.8 (t, J=6.1 Hz, 1H), 7.67 (d, J=8.2 Hz, 2H), 7.03 (broad s, 2H), 6.85 (broad t, J=6.3 Hz, 1H), 6.62 (d, J=8.2 Hz, 2H), 4.44 (d, J=6.5 Hz, 2H), 4.31 (m, 1H), 4.12 (d, J=2.2 Hz, 2H), 3.57-3.36 (m, 11H), 3.35-3.1 (m, 2H), 2.23 (t, J=7.2 Hz, 2H), 1.91 (m, 2H)

LCMS Characterization:
611 [M+H]+

3) Procedure for the Synthesis of FP547-Alkyne Triethylene Glycol (Preparation 2C)

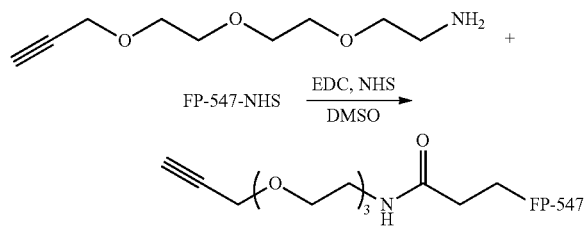

Experimental Procedure:
To a solution of FP-547-NHS (Interchim, 2.5 mg, 2.55 µmol, 1 equiv.) in DMSO (356 µL) was added a solution of DMSO (92 µL) containing EDC (0.49 mg, 1 equiv.), NHS (0.29, 1 equiv.), TEA (0.35 µL, 1 equiv.) and preparation 1E (1.07 mg, 2.2 equiv.).

The solution was stirred in the dark at room temperature for 12 hrs.

Treatment Process:
The reaction was concentrated under reduced pressure, dissolved into DCM and extracted with brine. A pink oil was obtained.

Ultraviolet Visible (UV/Vis) and Fluorescence Spectroscopy Characterization:
The spectra obtained were similar to the one given by the commercial source of the fluorophore compound.

Preparation 3: Synthesis of a Compound of Formula (II)

1) Procedure for the Synthesis of Benzyloxy-Azide PEG2500 (Preparation 3A)

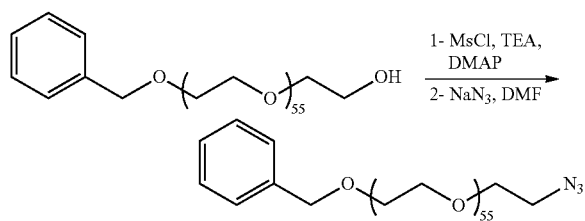

Experimental Procedure:
To a solution of PEG2500-benzyl (Polymer Source, $M_n$=2572 g·mol$^{-1}$, 2.43 g, 0.94 mmol, 1 equiv.), DMAP (58 mg, 0.5 equiv.) and TEA (747 µL, 5.6 equiv.) in DCM (65 mL), cooled down to 0° C., is slowly added MsCl (326 µL, 4.4 equiv.) over 20 min. The reaction is stirred overnight at room temperature and concentrated under reduced pressure. The residue is dissolved into DMF (20 mL) and sodium azide (330 mg, 5.3 equiv.) is added to the solution. The reaction is stirred at 50° C. for 24 hrs.

Treatment Process:
The reaction is concentrated under reduced pressure and the residue is dissolved into DCM (50 mL) and washed with brine (thrice with 50 mL). The organic layer is dried over MgSO$_4$, filtered and concentrated under reduced pressure to a minimum volume of DCM. The latter is precipitated into diethyl ether. 2.16 g of a white powder are obtained.

NMR Characterization:
$^1$H NMR (300 MHz, CDCl$_3$) δ 7.30-7.05 (m, 5H), 4.43 (s, 2H), 3.93-3.03 (m, 222H), 3.27 (t, 2H).

2) Procedure for the Synthesis of Azide PEG2500 (Preparation 3B)

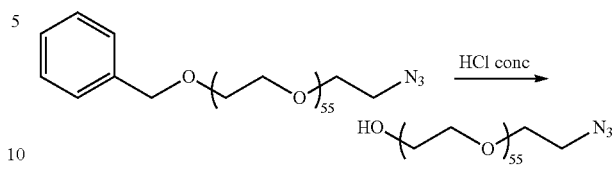

Experimental Procedure:
Preparation 3A (2.16 g, 0.83 mmol, 1 equiv.) is solubilized into HCl concentrated (20 mL) and stirred at room temperature for 2 days.

Treatment Process:
The solution is basified up to pH 1 with a solution of NaOH conc. The aqueous phase is extracted with DCM (four times with 50 mL) and the combined organic layers are dried over magnesium sulfate, filtered and concentrated under reduced pressure to a minimum volume of DCM. The latter is precipitated into diethyl ether. 1.89 g of a white powder is obtained.

NMR Characterization:
$^1$H NMR (400 MHz, CDCl$_3$) δ 3.73-3.33 (m, 222H), 3.27 (t, J=5.0 Hz, 2H), 2.75 (s, 1H).

3) Procedure for the Synthesis of Benzyloxy-Bromo PEG2100 (Preparation 3C)

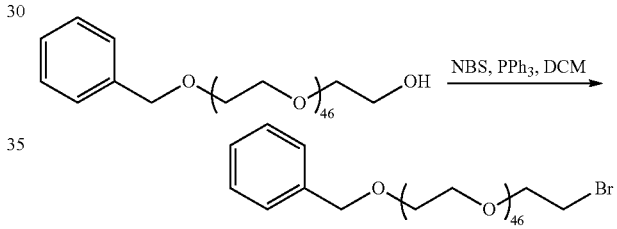

Experimental Procedure:
To a mixture of PEG2100-benzyl prepared in accordance with Nicolas et al. Macromol 2008, 41, 8418 ($M_n$=2176 g·mol$^{-1}$, 500 mg, 0.23 mmol, 1 equiv.) and NBS (50 mg, 1.2 equiv.) is added a cold solution of triphenyl phosphine (PPh3) (75 mg, 1.2 equiv.) into DCM (50 mL). The reaction is then stirred overnight at room temperature.

Treatment Process:
The reaction is concentrated under reduced pressure down to 25 mL and diluted with hexane (100 mL). The precipitate (triphenylphosphine oxide) is removed by filtration and the polymer is precipitated twice into diethyl ether (200 mL).

NMR Characterization:
$^1$H NMR (300 MHz, CDCl$_3$) δ 7.30-7.16 (m, 5H), 4.50 (s, 2H), 3.85-3.15 (m, 188H)

4) Procedure for the Synthesis of Bromo PEG2100 (Preparation 3D)

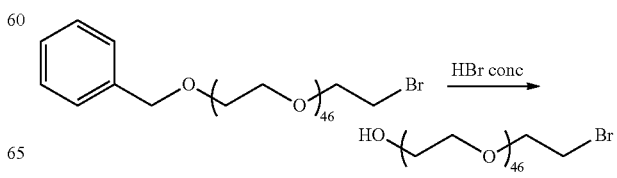

Experimental Procedure:

Preparation 3C (500 mg, 0.22 mmol, 1 equiv.) is solubilized into HBr concentrated (20 mL) and stirred at room temperature for 2 days.

Treatment Process:

The solution is basified up to pH 1 with a solution of NaOH conc. The aqueous phase is extracted with DCM (four times with 50 mL) and the combined organic layers are dried over MgSO$_4$, filtered and concentrated under reduced pressure to a minimum volume of DCM. The latter is precipitated into diethyl ether to obtain as powder form.

NMR Characterization:

$^1$H NMR (300 MHz, CDCl$_3$) δ 3.82-3.13 (m, 188H), 2.79 (s, 1H)

Preparation 4: Synthesis of a Compound of Formula (I)

Compounds of formula (I) have been synthesized using 2 different pathways. The first one (4A) is by one-step and the second one (4B) is by two steps.

Preparation 4A: Synthesis of Block Copolymer PLA-PEG-N$_3$ by Ring Opening Polymerization (ROP)

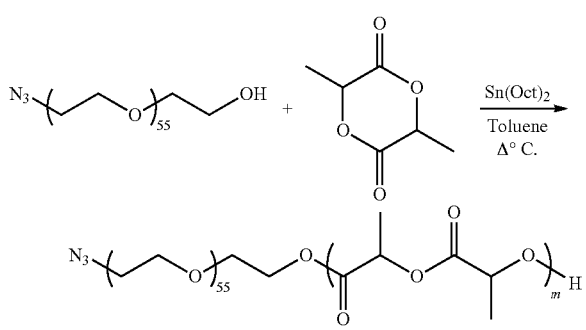

m being the number of PLA units

Experimental Procedure:

To a mixture of azido-poly(ethylene glycol) (3B, M$_n$=2507 g·mol$^{-1}$, 293 mg, 0.12 mmol) and D,L-Lactide (7.01 g, 48.62 mmol) was added, in dry conditions, a solution of Sn(Oct)$_2$ (18.7 mg, 46.1 μmol) in anhydrous toluene (11.2 mL). The reaction mixture was degassed by bubbling argon for 20 min and then stirred in a pre-heated oil bath at 120° C. for 90 min under inert atmosphere. The reaction was stopped at approximately 55% of conversion.

Treatment Process:

The toluene was removed under reduced pressure and the obtained product was dissolved into a minimum amount of DCM and further precipitated in diethyl ether. The precipitate was then dissolved into a minimum amount of THF and further precipitated in water and subsequently freeze-dried overnight to yield a white powder.

NMR Characterization:

$^1$H NMR (400 MHz, CDCl$_3$) δ 5.41-4.83 (m, 456H), 4.38-4.15 (m, 3H), 3.84-3.40 (m, 220H), 3.36 (t, J=4.8 Hz, 2H), 1.82-1.21 (m, 1372H).

TABLE 1

| Mn (theory) | Theory m (PLA unit) | Experimental Mn (NMR) | Measured m (PLA unit) |
|---|---|---|---|
| 62460 | 415 | 35340 | 228 |

Mn = Number average molecular weight determined by NMR
Theory: at 100% of conversion
NB: Different batches of the Preparation 4A polymer have been synthesized and used. The m value varies with each batch. m was typically between 180 and 250.

Preparation 4B(1): Synthesis of Block Copolymer PLA-PEG-Br by Ring Opening Polymerization (ROP)

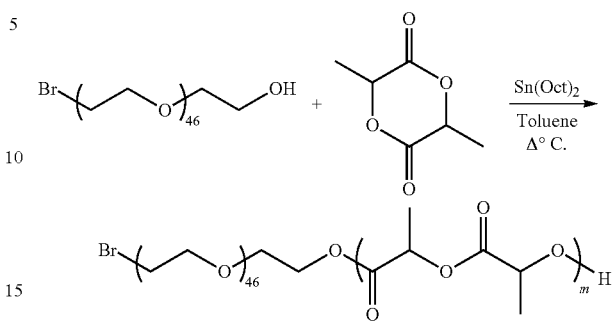

m being the number of PLA units

Experimental Procedure:

To a mixture of bromo-poly(ethylene glycol) (3D, M$_n$=2149 g·mol$^{-1}$, 49 mg, 22.8 μmol) and D,L-Lactide (0.72 g, 4.97 mmol) was added, in dry conditions, Sn(Oct)$_2$ (1 mg, 2.5 μmol). The reaction mixture was degassed with argon for 20 min and then stirred in bulk conditions in a pre-heated oil bath at 120° C. for 20 hours under inert atmosphere. The reaction stopped at full conversion.

Treatment Process:

The obtained product was dissolved into a minimum amount of DCM and further precipitated in diethyl ether. The precipitate was then dissolved into a minimum amount of THF and further precipitated in water and subsequently freeze-dried overnight to yield a white powder.

TABLE 2

| Mn (theory) | Theory m (PLA unit) | Experimental Mn (NMR) | Measured m (PLA unit) |
|---|---|---|---|
| 33510 | 218 | 34120 | 222 |

Mn = Number average molecular weight determined by NMR
Theory: At 100% of conversion
m = (Experimental Mn determined by NMR − Mn of PEG-Br)/MW of the lactide monomer = (34120 − 2100)/144 = 222
NB: The m value varies with each batch. m was typically between 100 and 300, more particularly between 180 and 250.

Preparation 4B(2): Procedure for the Synthesis of Azide-PEG2100-PLA

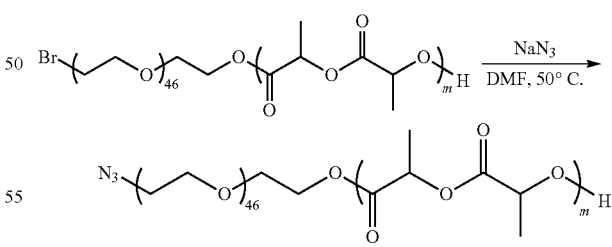

m defined as in the table above.

Experimental Procedure:

To a solution of preparation 4B(1) (200 mg, 5.9 μmol, 1 equiv.) in DMF (10 mL) is added sodium azide (20 mg, 54 equiv.) under inert conditions. The reaction is then stirred at 50° C. for 3 days under inert atmosphere.

$^1$H NMR (400 MHz, CDCl$_3$) δ 5.42-4.83 (m, 440H), 4.38-4.11 (m, 3H), 3.83-3.40 (m, 192H), 3.35 (t, J=4.8 Hz, 2H), 1.73-1.31 (m, 1320H).

Treatment Process:

The solution is concentrated under reduced pressure and the residue is solubilized into a minimum amount of THF. The latter is then precipitated into water.

Preparation 5: Synthesis of Compounds of Formula (A)

Typical procedure for the Huisgen reaction in organic conditions

NMR Characterization of PLA-PEG-Triazol-PEG'-Anisamide $^1$H NMR (500 MHz, CDCl$_3$) δ 8.31 (m large, 1H), 8.02 (s, 1H), 7.81 (d, J=8.1 Hz, 2H), 6.98 (d, J=8.1 Hz, 2H), 4.97-5.48 (m, 389H), 4.50 (s large, 4H), 4.10-4.26 (m, 3H), 3.80 (s large, 5H), 3.30-3.67 (m, 198H), 1.28-1.62 (m, 1164H)

Yield: 90% m being the number of PLA units, varying with each batch.

Example of Optimized Experimental Procedure:

To a previously degassed solution of compound of formula (I) PLA-PEG-N$_3$ prepared according to the method described for Preparations 4A (200 mg, molar quantity depending on the batch, in a representative case: 6.7 μmol, 1 equiv.) and alkyne derivative of formula (XI) (0.12 mmol, 18 equiv.) in anhydrous DMF (2.5 mL) was added, with a syringe, a degassed solution of CuBr (5.8 mg, 6.1 equiv.) and PMDETA (16.8 μL, 17.8 equiv.) in anhydrous DMF (400 μL). The reaction mixture was stirred for 15 hrs at 50° C. under inert atmosphere. The same methodology was used for all preparations.

Example of Optimized Treatment Process:

The solution was concentrated under reduced pressure and the residue was dissolved into a minimum amount of THF and further precipitated in water. The precipitate was freeze-dried, dissolved again into a minimum amount of THF and further precipitated in water. The precipitate was freeze-dried to yield a white powder.

If the alkyne derivative is insoluble into water then an intermediate step can be added by dissolving the first freeze-dried precipitate into a minimum amount of DCM and further precipitated in diethyl ether.

The last step should be a precipitation of THF into water. Also, purification steps can be added if some starting materials remain afterwards. The same methodology was used for all preparations in making a compound of formula (A) (see the following table 3).

Preparation 6: Synthesis of a Compound of Formula (I')

Procedure for the synthesis of block copolymer PLA-PEG-OMe by Ring opening polymerization (ROP)

m is the number of PLA units

Experimental Procedure:

To a mixture of methoxypoly(ethylene glycol) (Sigma-Aldrich, M$_n$=2012 g·mol$^{-1}$, 245 mg, 0.12 mmol) and D,L-Lactide (7.01 g, 48.62 mmol) was added, in dry conditions, a solution of Sn(Oct)$_2$ (18.7 mg, 46.1 μmol) in anhydrous toluene (11.2 mL). The reaction mixture was degassed by bubbling argon for 20 min and then stirred in a pre-heated oil bath at 120° C. for 30 min under inert atmosphere. The reaction was stopped at approximately 54.2% of conversion.

Treatment Process:

The toluene was removed under reduced pressure and the obtained product was dissolved into a minimum amount of

TABLE 3

| Ligand | Copo (mg) | Mn*$_{(Copo)}$ (g/mol) | Alkyne-ligand (mg) | Eq. of Alkyne | CuBr (mg) | Eq. of CuBr | PMDETA (μL) | DMF (mL) | Temp (° C.) | Time (h) |
|---|---|---|---|---|---|---|---|---|---|---|
| Anisamide | 200 | 35050 | 32.0 | 18.0 | 5.5 | 6.9 | 12.0 | 6.0 | 40 | 18 |
| Folic acid(*) | 200 | 29580 | 67.5 | 16.3 | 5.8 | 5.9 | 16.8 | 2.9 | 50 | 15 |
| FP-547 | 300 | 35050 | 3.0 | 0.3 | 6.0 | 5.1 | 18.0 | 4.0 | 50 | 15 |

(*)reaction conducted on the mixture of Compounds A and B of Preparation 2B
Mn*: Number average molecular weight determined by NMR
Copo: PLA-PEG-N$_3$
Eq: Equivalent DCM and further precipitated in diethyl ether. The precipitate was then dissolved into a minimum amount of THF and further precipitated in water and subsequently freeze-dried overnight to yield a white powder.

NMR Characterization:

$^1$H NMR (400 MHz, CDCl$_3$) δ 5.34-4.85 (m, 434H), 4.40-4.17 (m, 3H), 3.86-3.41 (m, 178H), 3.36 (s, 3H), 1.77-1.19 (m, 1302H).

TABLE 4

| Mn (theory) | Theory m (PLA unit) | Mn (NMR) | Measured m (PLA unit) |
|---|---|---|---|
| 59560 | 400 | 33260 | 217 |

Mn = Number average molecular weight determined by NMR
Theory: At 100% of conversion Example 2

Nanoparticle formation

Nanoparticles were prepared according to the following protocol and by using the components and amounts as specified in the following tables.

General Protocol

1—The copolymer or a mixture of copolymers is dissolved in the organic solvent (with a final aqueous polymer concentration varying between 1 to 40 mg/mL)

2—The organic phase is mixed with the aqueous phase (with an aqueous/organic volume ratio varying between 2.5 to 5) containing the stabilizer (concentration varying between 0.1% to 1% w/v). For the preparation of nanoparticles using emulsification and size reduction technique, the mixture is vigorously shaken using a vortex shaker for 1 minute to obtain an emulsion. The emulsion is sonicated (using a probe with a time varying from 1 to 10 minutes).

3—The organic phase is removed by evaporation (under reduced pressure or air flow)

4—The nanoparticles are ultracentrifuged at 30000 g for 30 minutes

5—The nanoparticles are resuspended in aqueous medium.

6—The nanoparticles are filtered over a 1 μm glass filter disc (Acrodisc).

7—The nanoparticles are stored at 4° C. until use.

As an Example the Following Protocol was Used where 1.2 Ml AcOEt were Used as Organic Solvent (See Last 3 Examples in Table 6 Below)

1—The copolymer or a mixture of copolymers (total mass: 30 mg) is dissolved in AcOEt (1.2 mL)

2—The organic phase is added to 3.3 mL of an aqueous phase containing 1% of Pluronic F68

3—The mixture is vigorously shaken with a vortex shaker for 1 minute

4—The emulsion is ultrasonicated (using a probe) for 3 minutes

5—The organic phase is removed under reduced pressure using rotary evaporator

6—The nanoparticles are ultracentrifuged at 30000 g for 30 minutes

7—The nanoparticles are resuspended in 3 mL of pH 7.4 phosphate buffered saline (PBS)

8—The nanoparticles are filtered over a 1 μm glass filter disc (Acrodisc).

9—The nanoparticles are stored at 4° C. until use

Nanoparticles were characterized using DLS (Dynamic Light Scattering) and an apparatus from Malvern (Zetasizer Nano ZS). Each copolymer mentioned in the tables below have a mean molecular weight comprised between 30000 Da and 35000 Da.

TABLE 5

Nanoparticles made of PLA-PEG-OMe and PLA-PEG-N$_3$ copolymer

| Copolymer (%) | | Organic Phase (ml) | | | Aqueous Phase (ml) | | | Final Copo concentration (g/L) | Characterization | | |
|---|---|---|---|---|---|---|---|---|---|---|---|
| PLA-PEG-OMe | PLA-PEG-N$_3$ | DCM | EtOAc | Acetone | (Na Cholate. %) | (PVA. %) | (Pluronic ®. %) | | Size (nm) | PdI | Zeta potential (mV) |
| 100 | | | | 6.7 | 12 (0%) | | | 2.8 | 33 | 0.22 | |
| 100 | | 2.3 | | | 11.7 (0.1%) | | | 1.2 | Precipitation | | |
| 100 | | 2.3 | | | 11.7 (0.2%) | | | 10 | 149 | 0.15 | |
| 100 | | 2.3 | | | 11.7 (0.5%) | | | 1.2 | 133 | 0.13 | |
| 100 | | 2.3 | | | 11.7 (1%) | | | 1.2 | 115 | 0.17 | |
| 100 | | 1 | | | 2.5 (1%) | | | 10.2 | 133 | 0.07 | |
| 100 | | 2.3 | | | | 11.7 (1%) | | 10 | 192 | 0.12 | |
| 100 | | 1 | | | | 2.5 (1%) | | 10.1 | 300 | 0.07 | |
| 100 | | 2.3 | | | | | 11.7 (1%) | 10 | Precipitation | | |
| 100 | | | 0.5 | | | | 2 (1%) | 15.4 | 174 | 0.12 | −8.7 |
| 100 | | | 1.2 | | | | 3 (1%) | 10.3 | 129 | 0.09 | −8.3 |
| 100 | | | 3 | | | | 7.5 (1%) | 4.1 | 109 | 0.16 | −7.2 |
| 100 | | | 1.2 | | | | 4.8 (1%) | 6.4 | 89 | 0.19 | −7.8 |
| 100 | | | 1.2 | | | | 3.3 (1%) | 9.3 | 108 | 0.12 | −6.6 |
| 83 | 17 | 2.3 | | | 11.7 (0.2%) | | | 9.9 | 148 | 0.14 | |
| 83 | 17 | 2.3 | | | | 11.7 (1%) | | 10 | 202 | 0.1 | |
| 90 | 10 | 1 | | | | 2.5 (1%) | | 10.1 | 227 | 0.1 | |
| 50 | 50 | 1 | | | | 2.5 (1%) | | 9.9 | 221 | 0.14 | |

The concentrations of the surfactants concentration indicated in the above table are in % w/v.
Pluronic ® = Pluronic F68; Copo = copolymer; PdI = Polydispersity Index
PVA = Polyvinyl alcohol) ~9500 Da
PLA = 30,000 Da (average); PEG = 2500 Da for PLA-PEG-N$_3$ and 2000 Da for PLA-PEG-OMe
PLA-PEG-OMe prepared according to preparation 6
PLA-PEG-N$_3$ prepared according to preparation 4A

TABLE 6

Nanoparticles made of PLA-PEG-Ligand copolymer blended or not with PLA-PEG-OMe copolymer

| PLA-PEG-OMe | PLA-PEG-Ligand Copolymer (%) Anisamide | Folic Acid | FP547 | Organic Phase (ml) DCM | EtOAc | Acetone | Aqueous Phase (ml) (Na Cholate. %) | (PVA. %) | (Pluronic ®. %) | Final Copo concentration (g/L) | Size (nm) | PdI | Zeta (mV) |
|---|---|---|---|---|---|---|---|---|---|---|---|---|---|
| 90 |  | 10 |  |  | 1 |  | 2.5 (1%) |  |  | 4 | 163 | 0.05 |  |
| 85 | 10 |  | 5 | 1 |  |  | 2.5 (1%) |  |  | 10.1 | 95 | 0.18 | −29 |
| 85 | 10 |  | 5 | 1 |  |  |  | 2.5 (1%) |  | 10.1 | 220 | 0.16 | −13.7 |
| 90 | 10 |  |  | 1 |  |  |  | 2.5 (1%) |  | 10 | 224 | 0.09 |  |
| 50 | 50 |  |  | 1 |  |  |  | 2.5 (1%) |  | 10.1 | 246 | 0.14 |  |
| 90 |  | 10 |  |  | 4 |  |  |  | 10 (1%) | 1 | 90 | 0.08 |  |
| 95 |  |  | 5 | 1 |  |  | 2.5 (1%) |  |  | 10 | 90 | 0.15 | −29 |
| 95 |  |  | 5 | 1 |  |  |  | 2.5 (1%) |  | 10 | 205 | 0.11 | −13.7 |
| 85 |  | 10 | 5 | 1 |  |  | 2.5 (1%) |  |  | 10.1 | 95 | 0.15 | −29 |
| 85 |  | 10 | 5 | 1 |  |  |  | 2.5 (1%) |  | 10.1 | 205 | 0.13 | −13.7 |
| 90 |  | 10 |  | 1 |  |  |  | 2.5 (1%) |  | 10 | 230 | 0.07 |  |
| 50 |  | 50 |  | 1 |  |  |  | 2.5 (1%) |  | 10.1 | 288 | 0.07 |  |
| 47.5 |  | 47.5 | 5 | 1 |  |  |  | 2.5 (1%) |  | 10.4 | 220 | 0.15 | −13.7 |
|  | 50 | 50 |  |  | 1.2 |  |  |  | 3.3 (1%) | 9.4 | 113 | 0.13 | −5.7 |
|  | 90 | 10 |  |  | 1.2 |  |  |  | 3.3 (1%) | 9.3 | 110 | 0.14 | −5.3 |
| 90 |  |  | 10 |  | 1.2 |  |  |  | 3.3 (1%) | 9.1 | 107 | 0.13 | −8.5 |
|  |  | 90 | 10 |  | 1.2 |  |  |  | 3.3 (1%) | 9.1 | 116 | 0.14 | −7.6 |

The concentrations of the surfactants concentration indicated in the above table are in % w/v.
Pluronic ® = Pluronic F68; Copo = copolymer; PdI = Polydispersity Index
PVA = Polyvinyl alcohol) ~9500 Da,
PLA = 30,000 Da (average); PEG = 2500 Da for PLA-PEG-N$_3$ and PEG = 2000 Da for PLA-PEG-OMe
PLA-PEG-OMe - preparation 6
PLA-PEG-Anisamide - preparation 5
PLA-PEG-Folic acid - preparation 5
PLA-PEG-FP547 - preparation 5

The tables above show that:
DCM/PVA led to physically stable nanoparticles with a 230 nm mean diameter range
EtOAc/NaCh resulted in physically stable nanoparticles with a 160 nm mean diameter range
EtOAc/Pluronic® led to physically stable nanoparticles with a 110 nm mean diameter range
The use of acetone resulted in micelles with a 30 nm mean diameter range Number of Ligands Per Nanoparticle:

$$Np = \frac{6\tau}{dp \cdot \pi \cdot D^3}$$

Np=Number of nanoparticles (NPs·L$^{-1}$ of suspension)
τ=solid content (g·L$^{-1}$)
D=average diameter (cm)
dp=polymer density (g·cm$^{-3}$)
For PLA polymers the average density is often cited as 1.24 or 1.27 g·cm$^{-3}$.
The average diameter is around 110 nm (1.1×10$^{-5}$ cm).
The solid polymer content is around 10 g·L$^{-1}$ for mother solution.
Therefore: Np~10$^{16}$ NPs·L$^{-1}$
Considering that the copolymer has a molecular weight of approximately 35000 g·mol$^{-1}$
Considering that the maximum concentration for folic acid on the surface of the nanoparticles (for the nanoparticles to be stable in pH 7.4 PBS solution) is around 30%.
The Avogadro number is N$_A$=6.022×10$^{23}$ mol$^{-1}$
Considering the data given above, there is per nanoparticle:
17000 copolymer molecules and 5100 folic acid molecules (if Mn$_{(copo)}$=35000 g·mol$^{-1}$)
20000 copolymer molecules and 6000 folic acid molecules (if Mn$_{(copo)}$=30000 g·mol$^{-1}$)

Example 3

Surface Plasmon Resonance (SPR) Using PLA-PEG-Folic Acid Nanoparticles

Series S Sensor Chip CM5 (GE Healthcare) Preparation
This sensor chip is covered with a matrix of carboxymethylated dextran covalently attached to the gold surface of the chip and composed of 4 channels.
Folate Binding Protein ((FBP), Sigma-Aldrich) Immobilization:
The protocol used for the immobilization of the protein is the one described by Johnson (Johnson et al *Anal. Biochem.* 1991, 198, 268-277). Briefly, after equilibration of the instrument with pH 7.4, PBS, the following samples were automatically and successively injected into the BIAcore T100: (i) NHS/EDC in a mixed solution (1:1, v/v) for 420 s to activate the carboxylated dextran; (ii) FBP dissolved at a concentration of 125 μg/mL in acetate buffer (pH 5.0) for 420 s, (iii) ethanolamine for 420 s to deactivate residual NHS-esters group on the sensor chip. Each step was punctuated with PBS washings. The immobilization protocol, which was performed at a flow rate of 10 μL/min, allowed the binding of ~6.8 ng/mm$^2$ of FBP per channel.
The first flow channel (Fc1) was blocked only by ethanolamine so it could be used as a reference channel in order to check whether or not the dextran is playing a role in the adsorption of nanoparticles.
Verification of the Immobilized FBP Conformation and Surface Regeneration:
In order to check if the immobilized FBP was in the right conformation a polyclonal antibody anti-FBP (IgG anti-FBP, Thermo Scientific) was used. The immunoglobulinG (IgG) was injected at 50 μg/mL for 120 s at 30 μL/min.
The specific signal is 4.5 times bigger than the non-specific signal (IgG on the reference channel Fc1) which represents approximately 22% of the total signal.

The use of glycine and ethylene glycol was considered to regenerate the surface. Indeed, it was possible afterwards to get a similar specific signal with the IgG anti-FBP.

Nanoparticle suspension was further tested on a freshly prepared protein-covered sensor chip channel.

Evaluation of the Interaction Between PLA-PEG-Folic Acid Nanoparticles and Immobilized FBP Surface Plasmon Resonance analyses of adsorption of PLA-PEG-Folic acid nanoparticles on immobilized FBP were performed using non-conjugated PLA-PEG nanoparticles as control. These experiments were conducted at a flow rate of 5 µL/min with a contact time of 500 s.

Nanoparticles Used:

Different suspensions of nanoparticles were prepared, using the previously described protocol (with Pluronic® as a stabilizer), with the aim of varying the concentration of folic acid at the surface of the nanoparticles. In order to do so, nanoparticles were prepared from a mixture of PLA-PEG-OMe ($Mn_{(NMR)}$=34820 g·mol$^{-1}$) and PLA-PEG-Folic acid ($Mn_{(NMR)}$=32880 g·mol$^{1}$).

TABLE 7

Summary of the characterization data of nanoparticles used for the SPR experiments:

| Sample | Folic acid (%) | Size (nm) | PdI | Zeta potential (mV) |
|---|---|---|---|---|
| 1 | 24 | 118.0 | 0.23 | −21.7 |
| 2 | 20 | 111.6 | 0.20 | −19.6 |
| 3 | 16 | 106.1 | 0.18 | −19.0 |
| 4 | 12 | 111.1 | 0.17 | −16.6 |
| 5 | 8 | 109.1 | 0.14 | −18.0 |
| 6 | 29 | 116.1 | 0.23 | −21.2 |
| 7 | 0 | 110.6 | 0.16 | −9.6 |

PdI: Polydispersity Index

The percentage of folic acid has been calculated from the amount of PLA-PEG-Folic acid used for each preparation and the yield of the click coupling between the alkyne-folic acid and the PLA-PEG-$N_3$. Beyond 30% of folic acid copolymer nanoparticles agglomerate.

Surface Plasmon Resonance Experiments:

Every nanoparticle suspension was tested on a freshly prepared protein-covered sensor chip channel.

Result Analysis:

The final values of the signals obtained from SPR sensorgrams of each sample were plotted on a graph against the concentration of folic acid on the nanoparticles (FIG. 4). Therefore, this graph shows the evolution of the specific signal relative to the concentration of folic acid at the surface of the nanoparticle. At 12%, a maximum is reached where the specific signal represent approximately 70% of the total signal. Beyond 12% the specific signal is decreasing. This can be due to some stacking between the different folic acid moieties thus preventing a better interaction. The non-specific signal is given by the value for nanoparticles having no folic acid on their surface.

As it is shown in the first 7 lines of the table, no matter which nanoparticles were injected in the reference channel, no signal is obtained. Therefore, the original coating surface (dextran) do not induce any adsorption of nanoparticles.

The non specificity is certainly due to the PEG coating of the nanoparticles with the FBP.

Example 4

Cytotoxicity

Example 4a

Cytotoxicity of PLA-PEG-Folic Acid Nanoparticles

In order to test these nanoparticles, KB-3-1 cell line (Human Cervix Carcinoma, DSMZ (German collection of microorganisms and cell cultures, catalog code: ACC 158) was used as it express folate receptors.

Cell Culture:

This is an adherent cell line growing in monolayers and cells were cultured in order to induce an over-expression of the folate receptors. The medium used to over-express the folate receptors was DMEM 2429 (medium without folic acid) in which L-Glutamine (200 mM at 0.584 g/L, BioWhittaker, Lonza) and sodium bicarbonate (3.7 g/L, Sigma-Aldrich) were added and supplemented with 1% penicillin/streptomycin (Lonza) and 10% fetal bovine serum (FBS, Lonza) in a 5% $CO_2$ humidified atmosphere at 37° C.

TABLE 8

Summary of conducted experiments:

| FC | Surface | Sample | $RU_{FBP\,Immob}$ | Dilution PBS | Copo Conc (g/L) | PLA-PEG-Folic (%) | Folic Conc (µM) | $RU_{Nanos}$ |
|---|---|---|---|---|---|---|---|---|
| 1 | Ref | 2 | 228 | 0.5 | 5.03 | 20% | 32.8 | |
| 1 | Ref | 3 | 228 | 0.5 | 5.00 | 16% | 25.8 | |
| 1 | Ref | 4 | 228 | 0.5 | 5.08 | 12% | 19.6 | |
| 1 | Ref | 5 | 228 | 0.5 | 5.04 | 8% | 12.9 | |
| 1 | Ref | 7 | 228 | 0.5 | 5.05 | 0% | 0.0 | |
| 1 | Ref | 6 | 228 | 0.5 | 5.06 | 29% | 48.0 | |
| 1 | Ref | 1 | 228 | 0.5 | 5.02 | 24% | 38.9 | 24 |
| 2 | FBP | 1 | 6627 | 0.5 | 5.02 | 24% | 38.9 | 1803 |
| 3 | FBP | 5 | 7723 | 0.5 | 5.04 | 8% | 12.9 | 2201 |
| 4 | FBP | 7 | 6865 | 0.5 | 5.05 | 0% | 0.0 | 1062 |
| 1 | FBP | 6 | 6368 | 0.5 | 5.06 | 29% | 48.0 | 2226 |
| 2 | FBP | 3 | 5626 | 0.5 | 5.00 | 16% | 25.8 | 2887 |
| 3 | FBP | 2 | 8249 | 0.5 | 5.03 | 20% | 32.8 | 1667 |
| 4 | FBP | 4 | 6008 | 0.5 | 5.08 | 12% | 19.6 | 3292 |

FC = Flow Channel
$RU_{FBP\,Immob}$ = Resonance Unit of immobilized FBP
$RU_{Nanos}$ = Resonance Unit of immobilized nanoparticle
Copo = copolymer
PBS = Phosphate buffered saline Nanoparticles Used:

Two different suspensions of nanoparticles were prepared, using the previously described protocol (with Pluronic® as a stabilizer), with the aim of having folic acid nanoparticles and control nanoparticles (no folic acid).

In order to do so, nanoparticles were prepared from a mixture of PLA-PEG-OMe ($Mn_{(NMR)}$=34820 g·mol$^{-1}$; 70% or 100% in weight) and PLA-PEG-Folic acid ($Mn_{(NMR)}$= 32880 g·mol$^{-1}$; 30% or 0% in weight respectively).

TABLE 9

Summary of the characterization data of nanoparticles used for the cytotoxic assay:

| Sample | Folic (%) | Size (nm) | Pdl | Zeta (mV) |
|---|---|---|---|---|
| S1 | 30 | 118.0 | 0.23 | −21.7 |
| S2 | 0 | 110.6 | 0.16 | −9.6 |

Cytotoxicity Assay Methodology:

In a 96 well plate, 5×10$^2$ cells diluted in 50 μL of culture medium (as described above) were deposited per well. After 24 h in a cell incubator, 50 μL of PBS buffer containing nanoparticles at different copolymer concentrations (0.5, 0.1, 0.05, 0.01 mg/mL) was added. The plate was then allowed to stand in a cell incubator (5% $CO_2$, 37° C.) for 48 h. Then, 20 μL of (3-(4,5-dimethylthiazol-2-yl)-5-(3-carboxymethoxyphenyl)-2-(4-sulfo-phenyl)-2H-tetrazolium) (MTS, a tetrazolium compound included in the CellTiter 96® AQ$_{ueous}$. Non-Radioactive Cell Proliferation Assay, Promega) was added and the plate was analyzed with a microplate reader (Labsystem Multiscan MS, Type 352) at 492 nm after. 3 hours of incubation in a cell incubator.

The data were compared to a well containing only 5×10$^2$ cells in 50 μL of culture medium and 50 μL of PBS buffer and revealed with 20 μL of MTS. From all data a background was removed consisting of nanoparticles, at the relevant concentration, in 50 μL of culture medium and 50 μL of PBS buffer and revealed with 20 μL of MTS. The experiments were performed in triplicate.

The plot was expressed as a function of a percentage of living cells, 100% being the well containing only cells and MTS.

Results:

Experiment performed with CellTiter 96® AQ$_{ueous}$ One Solution Cell Proliferation Assay (Promega) is illustrated on FIG. 5a.

It was observed that even at high concentration, no matter the presence or not of folic acid, nanoparticles do not induce any cytotoxicity on KB-3-1 cells over-expressing folate receptors.

Example 4b

Cytotoxicity of PLA-PEG-Anisamide Nanoparticles

In order to test these nanoparticles, PC-3 cell line (Human Prostate Adenocarcinoma, ATCC (Number: CRL-1435)) was used as it express sigma receptors to which the anisamide moiety could bind.

Cell Culture:

This adherent cell line was cultured in RPMI 1640 (Fisher Scientific) supplemented with 1% penicillin/streptomycin (Lonza) and 10% fetal bovine serum (FBS, Lonza) in a 5% $CO_2$ humidified atmosphere at 37° C. This cell line over-express sigma receptors. Cultures of 85-90% confluency were used for all of the experiments. The cells were trypsinized (Trypsin-EDTA, Invitrogen, Gibco), counted, sub-cultured into 96-well plates for viability studies. The cells were allowed to adhere for 24 h before using for experiments.

Nanoparticles Used:

Two different suspensions of nanoparticles were prepared, using the previously described protocol (with Pluronic®® as a stabilizer), with the aim of having fluorescent anisamide nanoparticles and fluorescent nanoparticle as control (no anisamide).

In order to do so, nanoparticles were prepared from a mixture of PLA-PEG-FP547 ($Mn_{(NMR)}$=34820 g·mol$^{-1}$; 10% in weight in both preparation), PLA-PEG-OMe ($Mn_{(NMR)}$= 34820 g·mol$^{-1}$; 45% or 90% in weight) and PLA-PEG-Anisamide ($Mn_{(NMR)}$=37060 g·mol$^{-1}$; 45% or 0% in weight respectively).

TABLE 10

Summary of the characterization data of nanoparticles used for the cytotoxicity assay:

| Sample | Anisamide (%) | Size (nm) | Pdl | Zeta (mV) |
|---|---|---|---|---|
| S3 | 45 | 119.7 | 0.20 | −8.9 |
| S4 | 0 | 111.7 | 0.11 | −9.1 |

Cytotoxicity Assay Methodology:

In a 96 well plate, 5×10$^3$ cells diluted in 50 μL of culture medium (as described above) were deposited per well. After 24 h in a cell incubator, 50 μL of PBS buffer containing nanoparticles at different copolymer concentrations (5, 2.5, 0.5, 0.05 mg/mL) was added. The plate was then allowed to stand in a cell incubator (5% $CO_2$, 37° C.) for 48 h. Then, 20 μL of (3-(4,5-dimethylthiazol-2-yl)-5-(3-carboxymethoxyphenyl)-2-(4-sulfo-phenyl)-2H-tetrazolium) (MTS, a tetrazolium compound included in the CellTiter 96® AQ$_{ueous}$ Non-Radioactive Cell Proliferation Assay, Promega) was added and the plate was analyzed with a microplate reader (Labsystem Multiscan MS, Type 352) at 492 nm after 3 hours of incubation in a cell incubator.

The data were compared to a well containing only 5×10$^3$ cells in 50 μL of culture medium and 50 μL of PBS buffer and revealed with 20 μL of MTS. From all data a background was removed consisting of nanoparticles, at the relevant concentration, in 50 μL of culture medium and 50 μL of PBS buffer and revealed with 20 μL of MTS. The experiments were performed in triplicate.

The plot was expressed as a function of a percentage of living cells, 100% being the well containing only cells and MTS.

Results:

Experiment performed with CellTiter 96® AQ$_{ueous}$ One Solution Cell Proliferation Assay (Promega) is illustrated on FIG. 5b.

It was observed that even at high concentrations of up to at least 5 mg/mL, no matter the presence or not of anisamide, fluorescent nanoparticles did not induce any cytotoxicity on PC-3 cells expressing sigma receptors.

Example 5

Cell Penetration Assay of PLA-PEG-Folic Acid Nanoparticles

In order to test these nanoparticles, KB-3-1 cell line (Human Cervix Carcinoma, DSMZ (German collection of microorganisms and cell cultures, catalog code: ACC 158) was used as it express folate receptors.

Cell Culture:

They are an adherent cell line growing in monolayers and they were cultured in order to induce an over-expression of the folate receptors. The medium used to over-express the folate receptors was DMEM 2429 (medium without folic acid) in which L-Glutamine (200 mM at 0.584 g/L, BioWhittaker, Lonza) and sodium bicarbonate (3.7 g/L, Sigma-Aldrich) were added and supplemented with 1% penicillin/streptomycin (Lonza) and 10% fetal bovine serum (FBS, Lonza) in a 5% $CO_2$ humidified atmosphere at 37° C.

Nanoparticles Used:

Three batches of 2 different suspensions of nanoparticles were prepared, using the previously described protocol (with Pluronic® as a stabilizer), with the aim of having fluorescent folic acid nanoparticles and fluorescent nanoparticles as control (without folic acid). In order to do so, nanoparticles were prepared from a mixture of PLA-PEG-FP547 ($Mn_{(NMR)}$=34820 g·mol$^{-1}$), PLA-PEG-OMe ($Mn_{(NMR)}$=34820 g·mol$^{-1}$) and PLA-PEG-Folic acid ($Mn_{(NMR)}$=32880 g·mol$^{-1}$).

The first batch (S1', S2') has been made 23 days prior to the second batch (S3', S4') and 34 days prior to the third batch (S5', S6').

TABLE 11

Summary of the characterization data of nanoparticles used for the cytotoxicity assay:

| Sample | OMe (%) | FP547 (%) | Folic acid (%) | Size (nm) | PdI | Zeta potential (mV) |
|---|---|---|---|---|---|---|
| S1' | 52.2 | 32.9 | 14.9 | 103.2 | 0.18 | −15.9 |
| S2' | 77.0 | 33.0 | 0 | 103.9 | 0.15 | −12.4 |
| S3' | 68.3 | 16.3 | 15.4 | 110.1 | 0.19 | −17.3 |
| S4' | 84.1 | 15.9 | 0 | 108.6 | 0.19 | −11.6 |
| S5' | 65.4 | 19.1 | 15.5 | 125.8 | 0.20 | |
| S6' | 81.0 | 19.0 | 0 | 117.8 | 0.21 | |

Fluorescence-Activated Cell Sorting (FACS) Methodology:

KB-3-1 cell line cultured in a medium to over-express their folate receptors (as mentioned above) were allowed to grow in a 24 well plate up to a near confluence (300000 cells/well). The culture medium is then removed and 1 mL of nanoparticles diluted into the same culture medium, at a final copolymer concentration of ~60 µg/mL, is incubated with the cells for a various amount of time (from 10 min to 24 hours). Afterward, the culture medium is removed, each well is washed twice with PBS buffer (1 mL) and the cells are detached with trypsin (200 µL for 3 min). The trypsin is then neutralized with culture medium (800 µL) and cells are centrifuged (5 min at 1000 g). The supernatant is removed, the cells are resuspended in PBS (1 mL), centrifuged (5 min at 1000 g) and finally recovered with paraformaldehyde (200 µL, 1% in PBS).

The flow cytometry study was achieved using a BD LSR-Fortessa cell analyser with an excitation wavelength of 561 nm and an emission signal retrieved between 575 and 589 nm.

Results:

The results obtained from the FACS experiments are illustrated in FIGS. 6a and 6b. It was observed that when folic acid is present at the surface of nanoparticles (S3'), the latter are 115 times more internalized than nanoparticles without folic acid (S4'). It was also observed that a plateau is reached between 6 and 10 hours of incubation.

It was also observed that the same results could be obtained with batches of 1 month old, 10 days old or 1 day old. Therefore, it can be concluded that folic acid nanoparticles are stable in time and that the folic acid moieties remain at the surface of the nanoparticles.

Example 6

Encapsulation of Docetaxel (DTX) into PLA-PEG-Anisamide Nanoparticles

To encapsulate docetaxel, the same protocol mentioned previously for the preparation of nanoparticles was used. Tritiated docetaxel was used during the process to evaluate the drug loading and the entrapment efficiency.

To 30 mg of copolymers (a mixture of PLA-PEG-OMe ($Mn_{(NMR)}$=34820 g·mol$^{-1}$; 60% in weight) and PLA-PEG-Anisamide ($Mn_{(NMR)}$=37060 g·mol$^{-1}$; 40% in weight)) diluted in 1.2 mL of ethyl acetate was added 2.8 mg of DTX (3.24 µmol; 861.9 g·mol$^{-1}$) and 4 nmol of $^3$H-DTX (5.38×10$^5$ Bq). This organic phase was mixed with 3.3 mL of an aqueous solution of pluronic F68 (1 wt/v %). The two phases were shaken vigorously with a vortex for 1 min and then sonicated with a probe for 3 min. Afterwards, the organic phase was removed under reduced pressure and the resulted aqueous phase was filtered through a 1 µm glass filter prior to ultracentrifugation (30 min at 30000 g). The supernatant was removed and the nanoparticles were resuspended into PBS buffer (10 mL) and filtered through a 1 µm glass filter.

Results:

The supernatant and the NPs solution were counted with a Beckman beta counter enabling to calculate a drug loading of 4.3% and an entrapment efficiency of 46%.

Example 7

Typical Procedure for the Huisgen Reaction in Aqueous Conditions for Carrying Out Click Chemistry onto the Preformed PLA-PEG-N$_3$ Nanoparticles

TABLE 12

| Ingredients | $Mn_{(NMR)}$ (Da) | Mass (mg) | Quantity (µmol) | Equiv | Volume (mL) |
|---|---|---|---|---|---|
| PLA-PEG-OMe | 42800 | 57.8 | 1.35 | 4.0 | |
| PLA-PEG-N$_3$ | 35400 | 12.0 | 0.34 | 1.0 | |
| PEG-alkyne | 2100 | 1.5 | 0.70 | 2.1 | |
| CuSO$_4$•5H$_2$O | 250 | 2.2 | 8.89 | 26.3 | |
| Na Ascorbate | 198 | 3.6 | 18.02 | 53.3 | |
| PVA | 9500 | 10.0 | 1.05 | 3.1 | |
| H$_2$O | 18 | | | 0.0 | 7.8 |

Experimental Procedure:

To a suspension of nanoparticles (made of PLA-PEG-N$_3$ (20% w/w) and PLA-PEG-OMe (80% w/w)) prepared following the previously described protocol and stabilized with poly(vinyl alcohol) (PVA) (1% w/v) was added PEG-Alkyne (2 equiv compare to the azido group), CuSO$_4$.5H$_2$O and sodium ascorbate (in excess).

The reaction mixture was stirred for 24 h.

Finally, the suspension was dialyzed against water using a cellulose membrane with a 20000 Da cutoff (SpectrumLabs).

Observation:

The size of the NPs suspension remains stable during the click process:

Z-average=198.5 nm and the PdI=0.09

In a similar way, other ligands (eg fluorescent ligands . . . ) can be bound to the nanoparticle according to the methodology described above.

The invention claimed is:
1. A compound of formula (A)

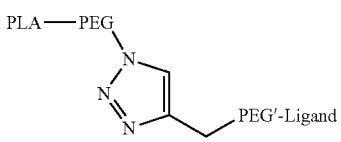 (A)

where:
PLA represents a polylactic acid rest;
PEG represents a polyethylene glycol rest;
the linker PEG' is a polyethylene glycol rest; and
Ligand is a functional ligand rest.

2. The compound of formula (A) according to claim 1, wherein PEG' is of formula

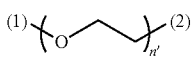

where:
n' is the number of units and is comprised between 1 to 10
(1) is the attachment of the bond to the —(CH$_2$)-triazole group;
(2) is the attachment of the bond to the ligand.

3. The compound of formula (A) according to claim 1, wherein PLA is of formula:

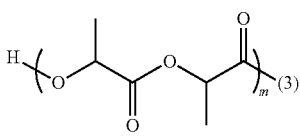

where:
(3) is the attachment of the bond to the PEG moiety; and
m is the number of units and is comprised between 1 and 500.

4. The compound of formula (A) according to claim 1, wherein PEG is of formula:

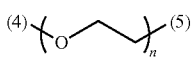

where:
(4) is the attachment of the bond to -PLA;
(5) is the attachment of the bond to the nitrogen atom of

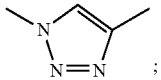 ;

and
n is the number of units and is comprised between 1 and 300.

5. The compound of formula (A) according to claim 1, wherein Ligand is chosen from rests of homing devices, diagnostic agents, imaging agents, stimuli-sensitive agents, docking agents, cell penetrating agents, detoxifying agents, and drugs.

6. The compound of formula (A) according to claim 5, wherein said homing device is a membrane recognition ligand.

7. The compound of formula (A) according to claim 1, wherein Ligand is chosen from:
a membrane recognition ligands selected from an oestrogen receptor antagonist, an androgen receptor antagonist, folic acid, anisamide, an antibody cabable of recognising the corresponding surface antigen, a RGD sequence that binds to α,β$_3$ integrins overexpressed on tumor angiogenic endothelium, hyaluronic acid, transferrin, peptide targeted gene vectors, aptamers, and tumor necrosis factor,
diagnostic/imaging agents selected from iron oxide, gadolinium complexes, indocyanin green, near infra-red fluorescent probes, and positron emitters,
stimuli responsive substances selected from iron oxide nanoparticles, gold nanoparticles, and any radiation-activable substances,
docking agents selected from oligopeptides,
a cell penetrating agent selected from Transactivator of transcription (TAT) sequences, penetratin, polyarginine sequences, and VP22 protein sequences,
a detoxifying agent selected from cobalamin, cobinamide, rhodanese enzyme, an organophosphorus hydrolyzing enzyme, naloxone, atropine, and antibodies/antibody fragments recognizing a specific toxin; and
a drug selected from an antibiotic, anti-cancer agent, anti-viral agent, anti-inflammatory agent, a vaccine antigen, and a nutraceutical.

8. A nanoparticle comprising one or more identical or different compounds of formula (A) according to claim 1.

9. The nanoparticle according to claim 8 which further comprises one or more compounds of formula (I'):

PLA_PEG_OR (I')

where PLA represents a polylactic acid rest; PEG represents a polyethylene glycol rest; and R is H or a C$_1$-C$_6$ alkyl.

10. A process for the preparation of the nanoparticle according to claim 8 comprising reacting a nanoparticle comprising one or more identical or different compounds of formula (I)

PLA_PEG_N$_3$ (I)

where PLA represents a polylactic acid rest; and PEG represents a polyethylene glycol rest,
with one or more compounds of formula (XI)

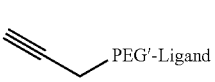 (XI)

where PEG' represents a polyethylene glycol rest and Ligand is chosen from rests of homing devices, diagnostic agents, imaging agents, stimuli-sensitive agents, docking agents, cell penetrating agents, detoxifying agents and drugs, optionally followed by non-covalent encapsulation or covalent conjugation of a drug.

11. A process for the preparation of the nanoparticle according to claim 8, comprising nanoprecipitating one or more compounds of formula (A)

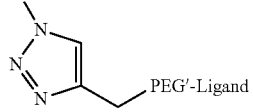 (A)

where PLA represents a polylactic acid rest; PEG represents a polyethylene glycol rest; the linker PEG' is a polyethylene glycol rest; and Ligand is a functional ligand rest, optionally in the presence of a compound of formula (I')

PLA_PEG_OR (I')

where PLA represents a polylactic acid rest; PEG represents a polyethylene glycol rest; and R is H or a C$_1$-C$_6$ alkyl, optionally followed by non-covalent encapsulation or covalent conjugation of a drug.

12. The nanoparticle according to claim 8 which comprises a drug.

13. The nanoparticle according to claim 12, wherein the drug is a cytotoxic agent.

14. The nanoparticle according to claim 12, wherein the drug is a taxoid.

15. The nanoparticle according to claim 12, wherein the drug is docetaxel.

16. The nanoparticle according to claim 12, wherein the drug is non-covalently encapsulated with the nanoparticle.

17. The nanoparticle according to claim 12, wherein the drug is covalently conjugated to the nanoparticle.

18. A pharmaceutical composition, which comprises at least one compound of formula (A) according to claim 1, optionally in the form of a nanoparticle comprising one or more identical or different compounds of formula (A).

19. A pharmaceutical composition, which comprises, as active principle, a compound of formula (A) according to claim 1, optionally in the form of a nanoparticle comprising one or more identical or different compounds of formula (A) and at least one pharmaceutically acceptable excipient.

20. A process for the preparation of a compound of formula (A) according to claim 1 comprising coupling:
a compound of formula (I):

PLA_PEG_N$_3$         (I)

with
a compound of formula (XI):

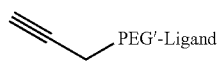

(XI)

where
PLA represents a polylactic acid rest;
PEG represents a polyethylene glycol rest;
PEG' is a polyethylene glycol rest; and
Ligand is a functional ligand rest.

21. The process according to claim 20, wherein said coupling is made by click chemistry.

22. The process according to claim 20, wherein said coupling reaction is carried out according to the Huisgen reaction, in organic or aqueous conditions.

23. The process according to claim 21, wherein said click chemistry coupling reaction is carried out in the presence of CuBr and PMDETA (N,N,N',N',N''-pentamethyldiethylenetriamine).

24. The process according to claim 21, wherein said click chemistry coupling reaction is carried out in the presence of water, CuSO$_4$5H$_2$O, and sodium ascorbate.

* * * * *